United States Patent [19]

Newkome et al.

[11] Patent Number: 5,585,457
[45] Date of Patent: Dec. 17, 1996

[54] METALLOSPHERES AND SUPERCLUSTERS

[75] Inventors: George R. Newkome; Charles N. Moorefield, both of Temple Terrace, Fla.

[73] Assignee: University of South Florida, Tampa, Fla.

[21] Appl. No.: 461,816

[22] Filed: Jun. 5, 1995

Related U.S. Application Data

[60] Division of Ser. No. 226,655, Apr. 12, 1994, Pat. No. 5,422,379, which is a continuation-in-part of Ser. No. 196,292, Feb. 11, 1994, which is a division of Ser. No. 116,912, Sep. 7, 1993, Pat. No. 5,376,690.

[51] Int. Cl.$^6$ ..................................... C08G 69/26
[52] U.S. Cl. ...................... 528/353; 528/171; 528/172; 528/173; 528/183; 528/351; 528/352
[58] Field of Search ................... 528/171, 172, 528/173, 183, 351, 352, 353

[56] References Cited

U.S. PATENT DOCUMENTS

| | | | |
|---|---|---|---|
| 4,435,548 | 6/1984 | Tomalia | 525/451 |
| 4,507,466 | 3/1985 | Tomalia | 528/332 |
| 4,558,120 | 12/1985 | Tomalia | 528/363 |
| 4,568,737 | 2/1986 | Tomalia | 528/332 |
| 4,587,329 | 5/1986 | Tomalia | 528/363 |
| 4,631,337 | 12/1986 | Tomalia | 528/391 |
| 4,694,064 | 9/1987 | Tomalia | 528/332 |
| 4,737,550 | 4/1988 | Tomalia | 525/418 |
| 5,154,853 | 10/1992 | Newkome | 252/311 |

OTHER PUBLICATIONS

Ringsdorf, "Molecular Architecture/Function of Polymeric Oriented Systems: Models for Study of Org., Surface Recognition and Dynamics of Biomembranes", *Angew Chem Ed. Engl.* 27:113–158 (1988).

Menger, "Groups of Organic Molecules That Operate Collectively", *Angew. Chem. Int. Ed. Engl*, 30:1086–1099 (1991).

Mekelburger et al., "Dendrimers, Arborols, Cascade Molecules: Breakthrough into Generations of New Materials", *Angew. Chem. Int. Ed. Engl.*, 31:1571–1576 (1992).

Tomalia, "Conformational Calculations on Plly–di–n–hexylsilane)" *Macromolecules*, 20:1167–1169 (1987).

Tomalia, "Starburst Dendrimers. 3. The Importance of Branch Junction Symmetry in the Dev. of Topological Shell Molecules", *J. Am. Chem. Soc.* 109:1601–1603 (1987).

Rengan and Engel, "Phosphonium Cascade Molecules", *J. Chem. Soc. Chem. Commun.* pp. 1084–1085 (1990).

Uchida, "General Strategy for Systematic Synthesis of Oligosiloxanes. Silicone Dendrimers", *J. Am. Chem. Soc.*, 112:7077–7079 (1990).

Wooley, "Polymers with Cont. Molecular Architecture: Cont. of Surface Functionality in Synthesis of Dendritic Hyperbranched Macromolecules" *J. Chem. Soc. Perkin Trans. 1* pp. 1059–1075 (1991).

Hawker and Frechet, "Preparation of Polymers with Contr. Molecular Architecture: A New Convergent Approach to Dendritic Macromolecules", *J. Am. Chem. Soc.*, 112:7638–7647 (1990).

Hawker and Frechet, "Control of Surface Functionality in Synthesis of Dendritic Macromolecules", *Macromolecules* 23:4726–4729 (1990).

Rajca, "Synthesis of 1,3–Connected Polyarylmethanes", *J. Org. Chem.* 56:2557–2563 (1991).

Rajca, "A Polyarylmethyl Carbotetraanion", *J. Am. Chem. Soc.*, 5889–5890 (1990).

Shahlai and Hart, "Supertriptycene, $C_{104}H_{64}$", *J. Am. Chem. Soc.* 112:3687–3688 (1990).

Pessi et al. "Appl. of Cont–flow Polyamide Method to Solid–phase Synth. of Multiple Antigen Peptide (MAP) based on Seq. of Malaria Epitope", *J. Chem. Soc. Chem. Commun.* pp. 8–9 (1990).

Padias et al., "Starburst Polyether Dendrimers", *J. Org. Chem.*, 52:5305–5312 (1987).

Moore and Xu, "Synthesis of Rigid Dendritic Macromolecules: Enlarging Repeat Unit Size as Function of Generation Permits Growth to Continue" *Macromolecules*, 24:5893–5894 (1991).

Lakowicz et al., "Time–Resolved Fluores. Anisotropies of Diphenylhexatrience and Perylene in Solvents and Lipid Bilayers Obtained from Multifreq. Phase–Modulation Fluorometry" *Biochem.* 24:376–383 (1985).

Menger et al., "Hexapus, a New complexing Agent for Organic Molecules" *J. Am. Chem. Soc.* 103:5938–5939 (1981).

Saunders and Hepler, "Localization of membrane–associated calcium following cytokinin treatment in Funaria using chlorotetracycline", *Planta* 152:272–281 (1981).

Schore, "Transition–Metal–Mediated Cycloaddition Reactions of Alkynes in Organic Synthesis", *Chem. Rev.* 88:1081–1119 (1988).

March, "Effects of Structure on Reactivity" *Advanced Organic Chemistry, Reactions, Mechanisms, and Structure,* Third Edition, pp. 237–301 (1985).

Nicalaou et al., "Synthesis and Chemistry of Dynemicin A Models", *J. Am. Chem. Soc.*, 113:3106–3114 (1991).

Nicholas and Pettit, "An Alkyne Protecting Group", *Tetrahedron Ltrs.* Pargamon Press, GB, 37:3475–3478 (1971).

(List continued on next page.)

*Primary Examiner*—Morton Foelak
*Attorney, Agent, or Firm*—Kohn & Associates

[57] ABSTRACT

Unimolecular micelies, generally referred to as cascade polymers, are constructed via the addition of successive layers, or tiers, of designed monomers, or building blocks, that possess a predetermined, branched superstructure consisting of connected physical matter inherently defining an internal void volume or void area within the molecular framework. Each of the branches define a flexible arm from a central core atom and terminate with a hydrodynamic reactive group. A method is described for manipulating such cascade polymers.

4 Claims, 11 Drawing Sheets

OTHER PUBLICATIONS

Exon and Magnus, "Stereoselectivity of Intramolecular Dicobalt Octacarbonyl Alkene–Alkyne Cyclizations: Short Synthesis of dl–Coriolin", *J. Am. Chem. Soc.* 105:2477–2478 (1983).

Magnus et al., "Synthesis of Remarkably Stable Bicyclo [7.3.1]diynene Esperamicin $A_1$/Calicheamicin $\gamma$ System", *J. Am. Chem. Soc.* 110:6923–6925 (1988).

Nicholas, "Chemistry and Synthetic Utility of Cobalt–Complexed Propargyl Cations", *Acct. Chem Res.* 20:214–221 (1987).

Bradley et al., "Surface Chemistry on Collodal Metals: High–Resolution Nuclear Magnetic Resonance Study of Carbon Monoxide Adsorbed on Metallic Palladium Crystallites . . . " *J. Am. Chem. Soc.* 113:4016 (1991).

Ketz et al., "Synthesis of Nido–Carbonate Containing Thioureas", *Tetrahedron Lett.* 31:4003–4006 (1990).

Miura et al., "Preparation of Carboranyl Porphyrins for Boron Neutron Capture Therapy", *Tetrahedron Lett* 31:2247 (1990).

Akitt, "Quadrupole Relaxation of Boron–11 and Boron–10 Nuclei" *J. Mag. Reson.* 3:411–414 (1970).

Nemoto et al., "Polyols of a Cascade Type as Water–Solubilizing Element of Carborane Derivatives for Boron Neutron Capture Therapy", *J. Org. Chem.*, 57–435 (1992).

Mittal et al., "The Wide World of Micelles", *Micellization, Solubilization, and Microemulsions*, vol. 1, pp. 1–21.

Tanford, "Micelles" *The Hydrophobic Effect: Formation of Micelles and Biological Membranes*, pp. 42–59 (1980).

Bochkov et al., "Synthesis of Cascadol, A Highly Branched Functionalized Polyether" translated from *Izvestiya Akademii Nauk SSSR*, Seriya Khimicheskaya, No. 10, pp. 2394–2395, (1989).

Kim, et al., "Water–Soluble Hyperbranched Polyphenylene: A Unimolecular Micelle", *J. Am. Chem. Soc.* 112, 4592–4593 (1990).

Miller et al., "Convergent Synthesis of Monodisperse Dendrimers Based upon 1,3,5–Trisubstituted Benzenes" *Chem. Mater.*, vol. 2 No. 4, 347–349 (1994).

Shinkai et al., "Hexasulfonated Calix[6]arene Derivatives: A New Class of Catalysts, Surfactants, and Host Molecules" *J. Am. Chem. Soc.* 198, 2409–2416 (1986).

Brooker and Sprague, "Color and Constitution. IV. The Absorption of Phenol Blue", *J. Am. Chem. Soc.* 63:3214–3215 (1941).

de Gennes et al., "Statistics of <<starburst>> polymers" *J. Phys. Letter,* 44:351–360 (1983).

Nicolas et al., "The Potential Utility of Transition Metal–Alkyne Complexes . . . " in *Transition Metal Organometallics Synthesis,* vol. II pp. 1–62 (1978).

Newkome et al., "Building Blocks for Dendritic Macromolecules" *Aldrichimica Acta,* 25:31–38 (1992).

Newkome et al., "Alkane Cascade Polymers Possessing Micellar Topology: Micellanoic Acid Derivatives" *Angew. Chem. Int. Ed. Eng.* 30: 1176–1180 (1974).

Newkome et al., "Platinum(0) Complexes of Heterocyclic Acetylenes . . . " *J. Am. Chem. Soc.*, 96:617–618 (1974).

Newkome et al., "Methyl Functionalization of Electron–Poor Heterocycles: Chloromethyl Derivatives of 2,2'–Bipyridines" *J. Org. Chem.*, 47:4116–4210 (1982).

Newkome et al., "Platinum(0) Complexes of Heterocyclic Acetylenes . . . " *J. Organometal Chem.*, 198:225–229 (1980).

Newkome et al., "Macrocyclic Inclusion Complexes. Synthesis, X–ray Structural Analysis . . . " *J. Org. Chem.*, 54:5105–5110 (1989).

Lee, H. W., *Dissertation*, Louisiana State University (1983) "The Syntheses of the Crown Ethers Possessing 2,6–Pyridino Moieties".

Tomasik, P. et al., "Phyridine Metal Complexes", *The Chemistry of Heterocyclic Compounds*, Part 6A–C, Interscience, Newkome and Strekowski, editors, New York (1985).

Newkome, G. R. et al., "Chemistry Within a Unimolecular Micelle: Metallomichellanoic Acids", *Polymer Preprints,* 1993, 34, 75.

Bruson, H. A. et al., "The Chemistry of Acrylonitrile. IV. Cyanoethylation of Active Hydrogen Groups" *J. Am. Chem. Soc.,* 64, 2457, 23–27 (1943).

Klausner, Y. S. et al., "Coupling Reagents in Peptide Synthesis" *Synthesis* 453–463 (1972).

DeTar, D. F. et al., "Reactions of Carbodiimides. III. The Reactions of Carbodiimides with Peptide Acids", *J. Am. Chem. Soc.* 88:5, 1024–1030 (1966).

Konig, W. et al., "Eine neue Methode zur Synthese von Peptiden: Aktivierung der Carboxyl mit Dicyclohexylcarbodiimid . . . " *Chem. Ber.* 103, 788–798 (1970).

Morris, K. F. et al., "Resolution of Discrete and Continuous Molecular Size Distributions by Means of Diffusion–Ordered . . . " *J. Am. Chem. Soc.* 115, 4291 (1993).

Gibbs, S. J. et al., "A PFG NMR Experiment for Accurate Diffusion and Flow Studies in the Presence of Eddy Currents" *J. Magn. Reson.* 93, 395–402 (1991).

Gibbs, S. J. et al., "Design and Implementation of a Shielded Gradient Coil for PFG NMR Diffusion and Flow Studies" *J. Magn. Reson.* 94, 165–169 (1991).

Stejskal, E. O. et al., "Spin Diffusion Measurements: Spin Echoes in the Presence of a Time–Dependent Field Gradient" *J. Chem. Phys.* 41(1) 288–295 (1965).

Kellomaki, A., "Galvanic Cells with Reacting Liquid Junctions . . . " *Chemical Abstracts,* vol. 83, No. 19, 170021p. (1975).

Moorefield, C. N., *Dissertation*, "Preparation, Characterization and Potential Applications of Cascade Polymers and Molecules" University of South Florida, (1991).

Tomalia, D. et al., "Dendritic Macromolecules: Synthesis of Starburst Dendrimers", *Macromolecules,* 19, 2466–2468 (1986).

Knudsen, M. et al., "Synthesis of the Angularly Fused Triquinane Skeleton via Intramolecular Organometallic Cyclization" *J. Org. Chem.* 4, 5025–5026 (1984).

Pilper, P. J., The Eur. J. Med. Chem. Chim., Ther,. p. 399 (1984).

Buhleier, E. et al., "Cascade– and Nonskid–Chain–like Syntheses of Molecular Cavity Topologies" *Synthesis,* 155–158 (1978).

Newkome, G. et al., "Syntheses, Reactions, and Applications" *Contemporary Heterocylic Chemistry,* 177–178 (1982).

Kauffmann, T. et al., "Nucleophile Akylierung und Arylierung des 2,2'–Bipyridlys", *A. Chem. Ber.* 109:3864–3868 [not translated; only copy available] (1987).

Bochkarev, M. N., et al., "Polyphenylenegermane—a new type of polymeric" *Journal on Organometallic Chemistry,* 195–200 (1987) [not translated; only copy available].

Singh, S. et al., "Extensions of Bicycloalkyne Trimerizations" *J. Org. Chem.* 1990, 55, 3412–3415.

Hawker, C. et al., "A New Convergent Approach to Monodisperse Dendritic Macromolecules" *J. Am. Chem. Commun.* 1010–1013 (1990).

R=CH$_2$OCH$_2$C$_6$H$_5$

3

1

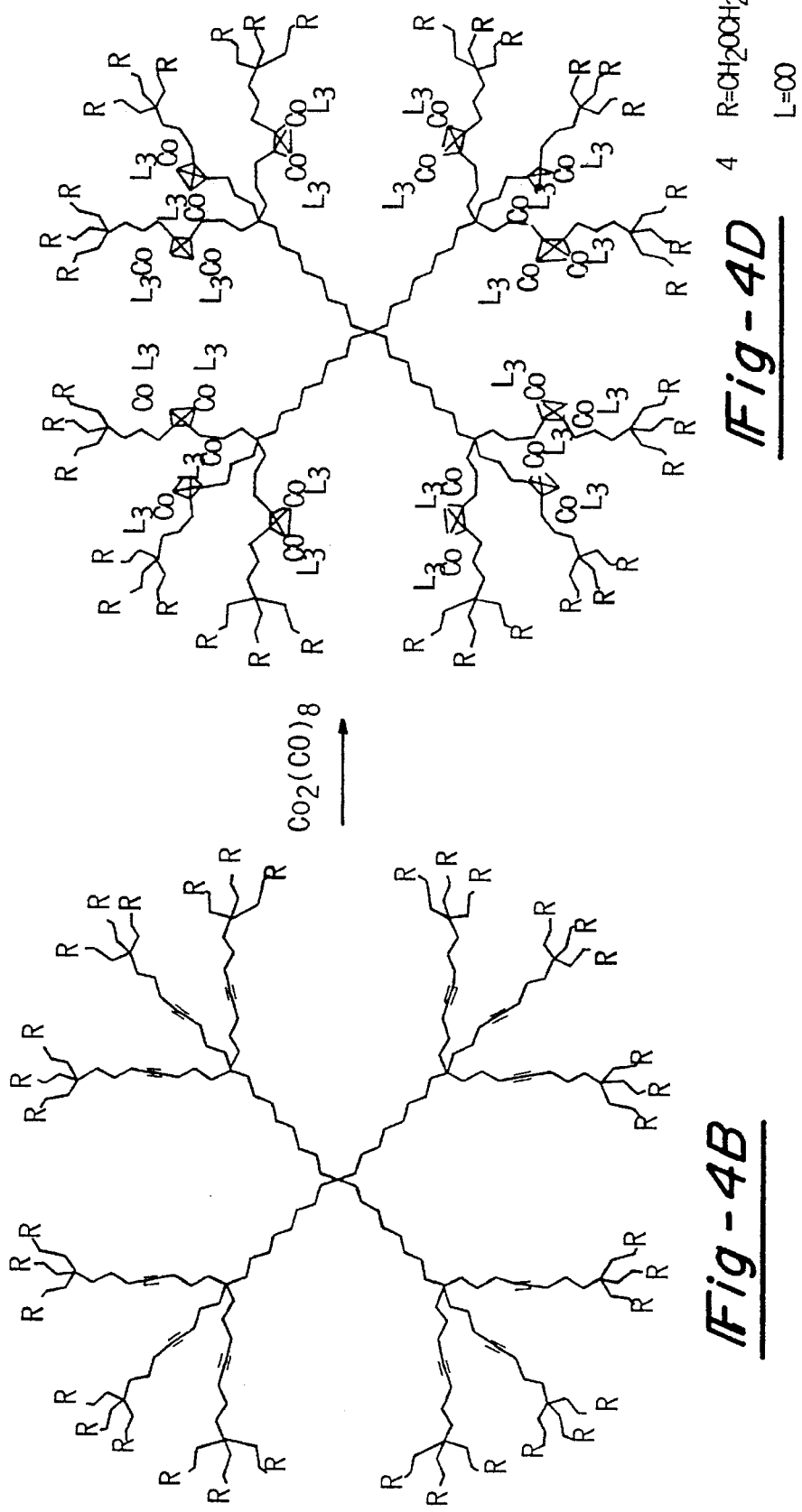

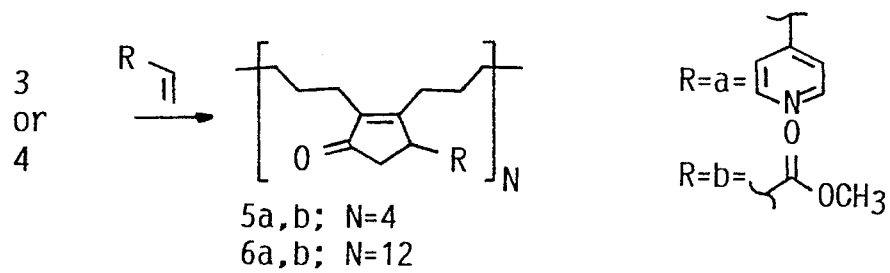
*Fig-4E*
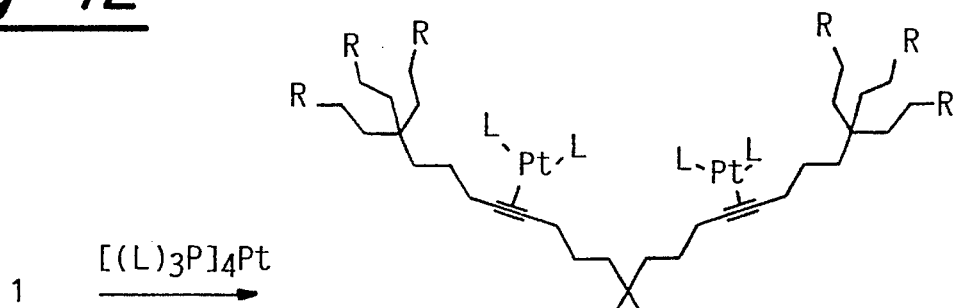
*Fig-5A*
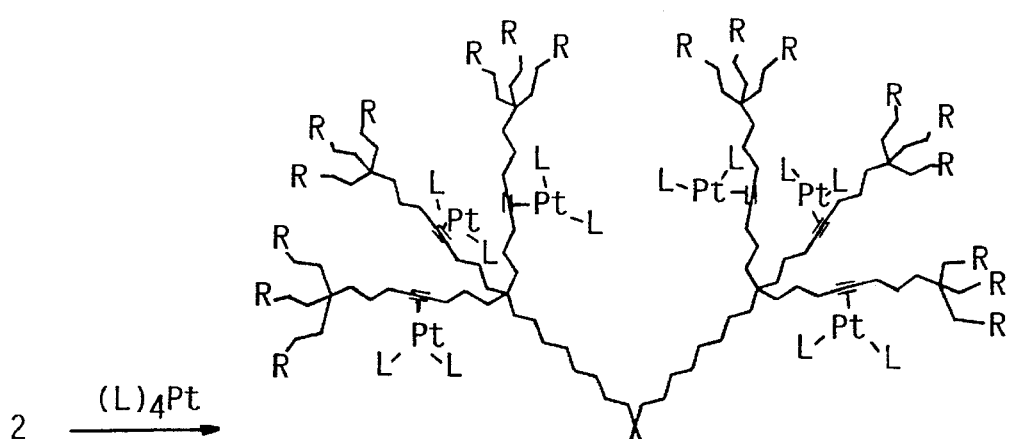
*Fig-5B*
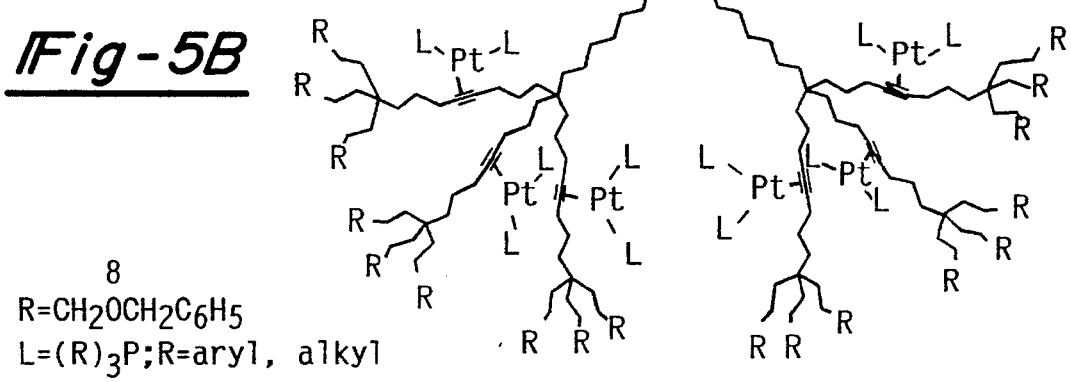

R = CH$_2$OCH$_2$C$_6$H$_5$

14

R = CH₂O₂C₆H₅

METALLOSPHERES AND SUPERCLUSTERS

This is a divisional of application Ser. No. 08/226,655 filed on Apr. 12, 1994; now U.S. Pat. No. 5,422,379 which is a CIP of Ser. No. 08/196,292 filed Feb. 11, 1994; which is a divisional of Ser. No. 08/116,912 filed Sep. 7, 1993, now U.S. Pat. No. 5,376,690, issued Dec. 27, 1994.

TECHNICAL FIELD

The present invention relates to highly-branched molecules possessing a predetermined three-dimensional morphology, referred to as unimolecular micelies. More specifically, the present invention relates to micelles having uses in areas such as radio-imaging, drug delivery, catalysis, size standards for chromatography and the like and other areas.

BACKGROUND OF THE INVENTION

Neat and orderly arrays for micellar systems have been reported,[1,2] and are structurally based on the original work of Vögtle et al., [3a] who delineated "cascade" construction The U.S. Pat. Nos. 4,435,548, issued Mar. 6, 1984; 4,507,466, issued Mar. 26, 1985; 4,558,120, issued Dec. 10, 1985; 4,568,737, issued Feb. 4, 1986; 4,587,329; issued May 6, 1986; 4,631,337, issued Dec. 23, 1986; 4,694,064, issued Sep. 15, 1987; and 4,737,550, issued Apr. 12, 1988, all to Tomalia et al., relate to branched polyamidoamines. The polyamidoamines include a plurality of pendent aminoamide moieties exhibiting properties which are related to linear polyamidoamines from which the branched polymers are derived. These compounds can be characterized as high molecular weight, highly-branched, multi-functional molecules possessing a three-dimensional morphology. Synthetic strategies employed for the realization of such "cascade polymers"[3b] require consideration of diverse factors including the content of the initial core, building blocks, space for molecules, branching numbers, dense packing limits, and desired porosity, as well as other factors.[4] The selection of the building blocks govern the type of branching desired from the core molecule, as well as the technology used to attach each successive layer or "tier" of the cascade polymer.

Applicants have developed a novel method of making cascade polymers, especially those providing a unimolecular micelle consisting essentially of alkyl carbon possessing diverse terminal functionality. Such compounds are disclosed in U.S. Pat. No. 5,154,853 (1992) to applicants.

Further developments of the above-described chemistry by applicants have demonstrated that the unimolecular micellar character permits the initial evaluation of the orderliness and chemistry within a series of specifically designed, spherical macromolecules due to covalently bound assemblies of internal reactive sites.[5,6] Similar dendritic species have been constructed with amide,[4,7,8] ethereal,[9,10] phosphonium,[11] silicone,[11,12] germane,[13] and aryl,[14–19] inner linkages and functionalities.

Out of all these systems, however, it has been determined that only three systems thus far created have the potential to undergo specifically located chemical modification within the inner lipophilic regions thereof. When there is actual space within these regions, these lipophilic regions are termed "void regions". The sum of the "void regions" constitutes the total "void volume" of the cascade polymer. The presently known compounds having such inner void regions capable of covalent modification are the hydrocarbon-constructed cascade intermediates possessing specifically located internal substituents or unsaturated centers, e.g., dialkylacetylenic moieties, set forth in the above-captioned patent to applicants (U.S. Pat. No. 5,154,853), those compounds disclosed by Moore and Xu,[19] that possess rigid polyalkyne spacers, or connectors, between branching centers and are thus prone to incomplete chemical transformations, and hence asymmetry, due to stearic interactions, and those compounds set forth in the Tomalia patents set forth above which are amino-branched compounds having short linkages between branch points (thus minimizing void volume) and internal bridging trialkyl substituted nitrogen atoms possessing less than pure $sp^3$ hybridization, making internal nucleophilic substitution difficult.

Critically, applicants have found[6] that the dialkylacetylene moieties of the cascade polymers set forth herein are also specifically located within accessible void regions. Applicants have shown that molecular guest probes, including diphenylhexatriene (DPH), phenol blue (PB), naphthalene, chlortetracycline (CTC), and pinacyanol chloride (PC) can be used as micellar probes to access the infrastructure of such cascade polymers utilizing known chemistry.[20–24]

Applicants' demonstrations of accessibility of void regions to chemical modification has led to the development of the ability to manipulate internal moieties within the spherically symmetrical dendritic macromolecule, after construction, to allow easy incorporation of internally located sensitive and/or reactive groups which otherwise would be difficult to introduce or protect during cascade construction. Specifically, the introduction of metal and metalloid centers at the interior of cascade infrastructures has been accomplished. Such derived compounds, referred to generically as metallospheres, superclusters, unimolecular Metallomicellanes and Nonmetallomicellanes, Metalloidomicellanes, derivatized Micellanes, or Micellanes, can be utilized for drug delivery of various metals and nonmetals, which are presently difficult to deliver in pharmacologically efficacious matters. The use of carrier-metal combinations as pharmacotherapeutic agents has had the problem of not being able to deliver sufficient metal/nonmetal to a site at a sufficiently low dose of the carrier of the metal/nonmetal per se. The present invention provides a means of delivering high concentrations of the metal/nonmetal moiety(ies) to a site at a relatively low dose of carrier (Micellane system).

Accessibility to void regions can be achieved by various means. Accessibility can be achieved during synthesis of tiers of the macro-molecular or can be achieved after synthesis by various manipulations of the molecule. It has been found that these manipulations of the molecule can be achieved by increasing and then, decreasing the size of the molecule. Accordingly, these size increases and decreases can be controlled, then the present invention can relate to areas of molecular size standards, such as those used for chromatography and the like. Based on the aforementioned research, applicants have found that the specific chemical nature of the micelle constructed in accordance of the present invention. Those allowed them to be adapted for manipulation of size to be used as a standard size marker. Further, the molecules can be preferentially constructed to allow for a specific size changes dependant upon branch arm flexibility, terminal groups, and the nature of the environment about the molecules.

SUMMARY OF THE IVENTION AND ADVANTAGES

In accordance with the present invention, there is provided a method of manipulating a unimolecular micelle in an environment wherein the micelle includes at least one core atom and arms branching from the core atom forming an outer surface of the micelle. The method includes the steps of reversibly changing the solubility of the outer surface of the micelle in the environment while reversibly extended the arms of the micelle to expand and contract the micelle. The present invention further provides a method of preparing a unimolecular micelle by the general steps of forming a core atom having a plurality of flexible branching arms extending therefrom and terminating each arm with a hydrodynamic reactive group.

The present invention further provides a unimolecular micelle consisting essentially of a core atom and a plurality of flexible arms extending therefrom, each of the arms terminating with a hydrodynamic reactive group.

BRIEF DESCRIPTION OF THE DRAWINGS

"The file of this patent contains at least one drawing executed in color. Copies of this patent with color drawing(s) will be provided by the Patent and Trademark Office upon request and payment of necessary fee."

Other advantages of the present invention will be readily appreciated as the same becomes better understood by reference to the following detailed description when considered in connection with the accompanying drawings wherein:

FIG. 5 shows the preparation of a unimolecular Platinomicelle, which possesses multiple platinum centers within the lipophilic core;

DETAILED DESCRIPTION OF THE INVENTION

Figure 1A:
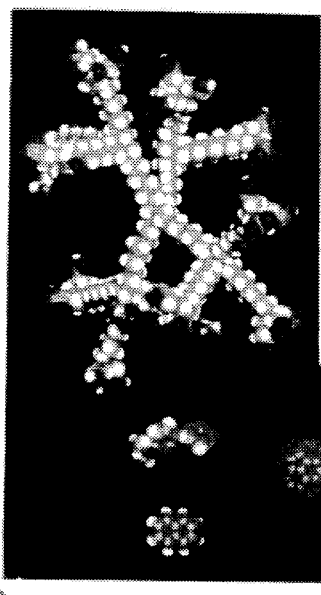
FIG. 1 shows expanded and contracted views of the second tier of a representative Micellane model and various guests and probe molecules.

The present invention provides a unimolecular micelle including internal void areas, the void areas including reactive sites capable of covalent and noncovalent bonding to guest(s). The unimolecular micelles of the present invention are cascade polymers which act as micelies. Such unimolecular micelles can be generally in the form of those disclosed in U.S. Pat. No. 5,154,853 to applicants, cited above, being all alkyl molecules, or in the form of those disclosed in the Tomalia patents discussed above, having a nitrogen core or branching site. Such compounds have pre-defined branching, depending upon the number of sequential tier additions that are performed in accordance with the above-cited references. The etymology of the term "Micelle", as employed in the classical or usual sense, refers to a noncovalently associated collection (aggregate) of many simple molecules functioning as a unit having unique properties (e.g., aqueous solubilization of water insoluble materials) that are not observed with the individual molecules which comprise the micelle; whereas as used herein, unimolecular micelle or micellane refers to a single macromolecule, possessing a covalently constructed superstructure, that can perform the same function(s)[6] as a classical micelle. Additions to these terms denote the incorporation of specific types of metals or nonmetals within the chemically accessible lipophilic interior of the unimolecular micelle. The term ligand is meant to describe any site that has the ability to donate electron density, such as a pair of electrons to a metal or nonmetal moiety, thus forming a covalent or noncovalent bond. Most often the term is used when discussing metals that are bonded, or complexed, to atoms, such as N, P, 0, and/or S. The term guest(s) is (are) meant to describe any metal or nonmetal (or any reasonable combination thereof) specie(s) that can be introduced into or onto the cascade framework. The introduction can be irreversible due to the formation of covalent bonds or reversible due to the formation of noncovalent bonds that are easily broken (e.g., hydrogen bonds) or the reversibility may be due to lipophilic-lipophilic and hydrophilic-hydrophilic attractions.

Micelles made in accordance with the present invention can be described as having at least one core atom, preferably a carbon atom, and arms branching from the core atom. The terminations of the arms or with larger branching, possibly mid-portions of the arms may fold to form an outer surface of the micelle. The surface of the micelle is exposed to immediately surrounding environment in which the micelle is disposed. This environment will have a certain hydrodynamic character, determined by properties such as pH, lipophilicity-hydrophilicity characteristics.

The surfaces of the micelles can be readily coated with metal ions. Mono-, di-, and trivalent metals are being possibly bonded directly or indirectly through terminal carboxyl groups or the like, similar to the dissolution of metal ions by most micellar or acidic systems.

The micelles can be characterized as having branches or arms which can be flexible, each of the arms terminating with a hydrodynamic reactive group. The term "flexible"

means that the arms are capable of extending away from and then, in reverse, folding towards the core atom. Flexibility further describes the relativeability of these arms to extend and contract relative to the core arm. Thusly, as discussed below, the branches or arms can be chemically altered such that the arms or branches can extend further or shorter from the core atom thereby controlling the ability of the micelles to expand in a given environment having no hydrodynamic characteristics. In combination with the flexibility of the arms or branches, the nature of the terminal groups can also effect the expansion of the micelle in different environments. Thusly, the selection of specific hydrodynamic reactive groups can effect the relative expansion and contraction of the hydrodynamic radius of these molecules.

The term "hydrodynamic reactive group" refers to chemical groups which can be bound to the terminal ends of arms or branches which are reactive with outer environment based on the hydrodynamic character of the environment. For example, groups such as alcohols, amines, carboxyls, thiols, phosphines, ammonium ions, sulfoniums ions, phosphonium ions, nitrates, sulfates, phosphates, and carboxylates, as well as other known reactive groups can be modified depending upon the hydrodynamic character of the surrounding environment. For example, hydrodynamic changes such as pH can protonate and deprotonate carboxyls and amines and thereby change the solubility characteristics of these reactive groups in the environment. Increased solubility in combination with flexibility of the arms or branches of the micelle will result in expansion of the arms and the concomitant effective increase in hydrodynamic radius of the micelle. Essentially, the molecule becomes larger. Decreases in the solubility will likewise contract the molecule.

It has been found that with significant increases in length of branches or arms, the arms or branches may fold into the micelle thereby not necessarily exposing the terminal end of the arm or branch but rather, a mid-section. Accordingly, hydrodynamic groups exposed in this manner can also effect expansion and contraction of the micelle.

As discussed below, this character of the micelles made in accordance of the present invention provides for a wider range of uses of the micelies.

The alkylcarbons surrounded by the branched arms of the micelles define a core therewithin. The above-cited patent discloses the incorporation of nitrogen, oxygen, sulfur, or phosphorus molecules into the molecular core. The molecules are seated within the void regions of the infrastructure, but not chemically bound therein. It is further possible to incorporate chirality into either the core region or on the surface, thereby creating a chiral sphere with an objectively active surface and/or interior possessing the ability to resolve and recognize chiral molecules.

The above-cited patent discloses that unimolecular micelles made in accordance with the present invention have a porosity which is predetermined, created by the relationships of the branches, the core defined above, and each of the quaternary areas or tertiary centers (carbon core or nitrogen branching sites, respectively) and created by each additional tier layered thereon. The porosity of the inside core can be changed by increasing or decreasing the distances between the quaternary or tertiary centers; that is, by changing the branch arm lengths.

As discussed above, the surface character of the micelles made in accordance with the present invention can be varied. For example, a carboxyl surface can be created, thereby rendering the micelles useful for detergents and surfactants, and also reactive to pH.[25] Changes in pH which increase the solubility of the surface components can expand the dendritic arms, thereby allowing accessibility to the void regions of the unimolecular micelle. Returning the pH to its original character can then contract the dendritic arms, thereby once again enclosing the void regions. This method of changing solubility of the unimolecular micelles by changing the environment in which the unimolecular micelles are retained can be used to provide accessibility to the void regions for chemical modification, as discussed in detail below.

Besides carboxyl groups, hydroxyl groups, and amines, other acidic, neutral, and/or basic functionalities can be incorporated onto the surface or on interior dendritic arms adjacent to the void regions of these unimolecular micelles as set forth in U.S. Pat. No. 5,154,853. The void areas of these unimolecular micelles made in accordance with the present invention have been characterized. The expanded and contracted nature of such dendritic arms defining the micelles have also been characterized.

Figure 1B:
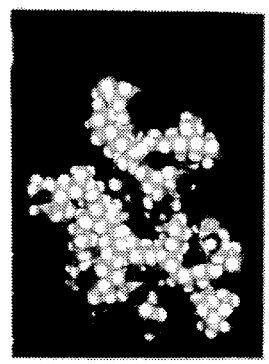

FIG. 1 shows the expanded and contracted views of the second tier of acidic coated unimolecular micelles made in accordance with the present invention, as well as depicting the void regions, and, hence, the total void volume, located within the cascade infrastructure. Non-bonded molecular guests that have been shown to be incorporated include, but are not limited to, diphenylhexatriene (DPH), phenol blue (PB), naphthalene, chlortetracycline (CTC), and/or pinacyanol chloride (PC).

Figure 2A:
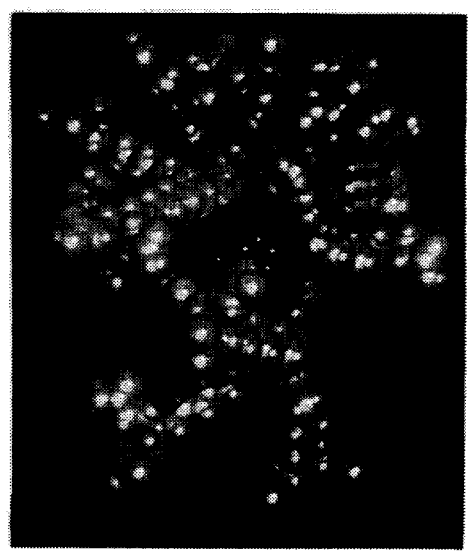
FIG. 2 shows a computational demonstration of the non-bonded incorporation of various molecular probes within the representative Micellane as illustrated in FIG. 1: (a) buckminsterfullerene, (b) diphenylhexatriene, (c) chlortetracycline, and (d) naphthalene.
Figure 2B:
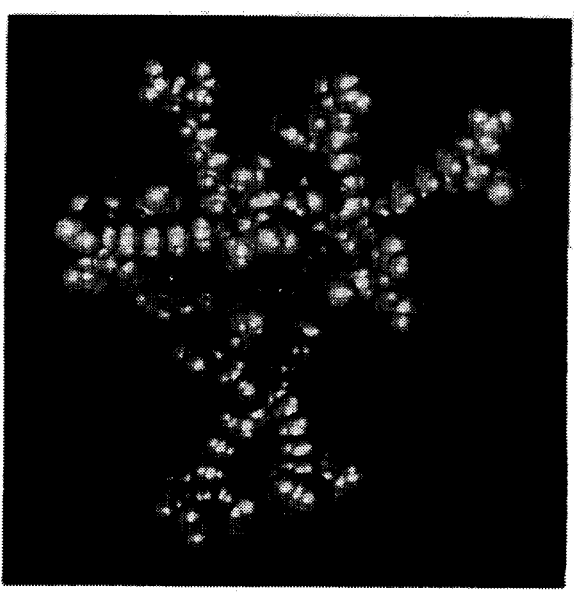
Figure 2C:
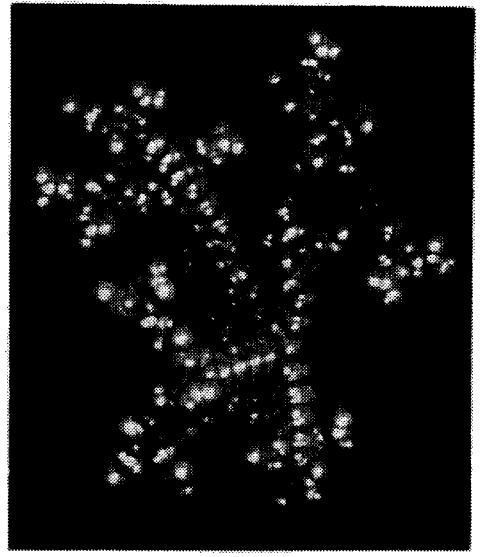
Figure 2D:
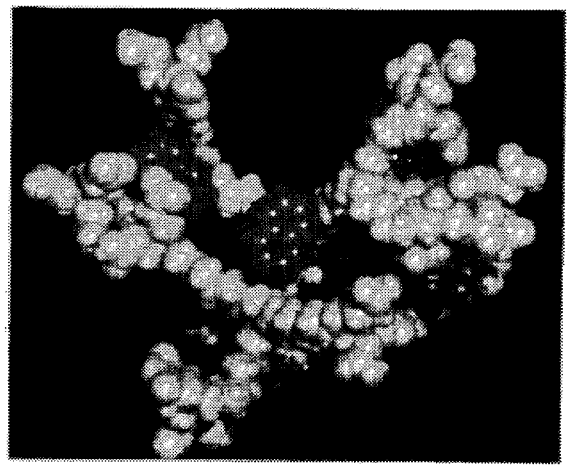

The sizes of the void regions have been demonstrated computationally by the incorporation of a 9 Å $C_{60}$ buckminsterfullerene, as shown in FIG. 2A. As shown, four such spherical guest(s) can be conveniently hosted within the molecule shown in FIG. 1. FIG. 2 further shows other previously used probes to be docked in a partially-expanded molecule as shown in FIG. 1 to demonstrate the porosity of these unimolecular micelies. As tier growth continues, these void areas are incorporated and engulfed, but are not totally filled, such that construction is totally analogous to the growth of a cauliflower, a point previously made by de Genees to describe N-bridged dendritic species.[26]

Figure 3A:
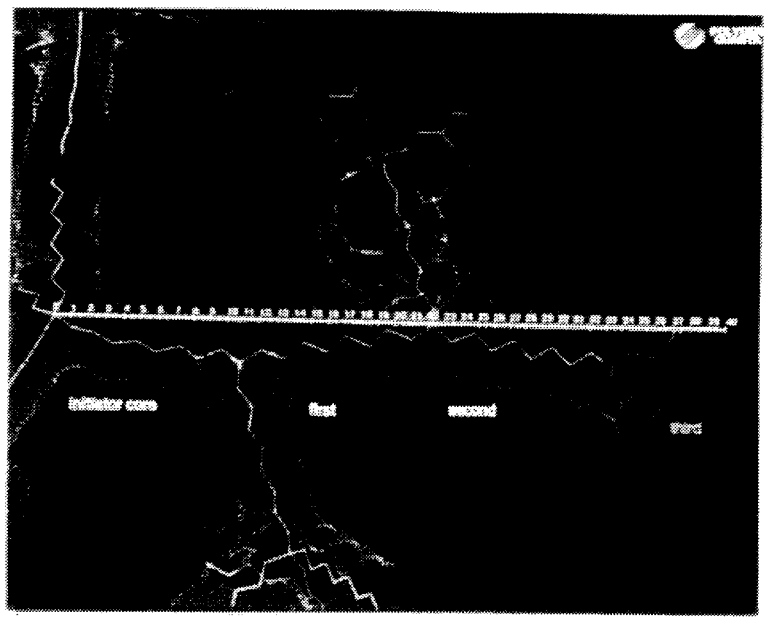
FIG. 3 shows a segment of an extended view of a third tier homolog of the unimolecular micelle depicted in FIG. 1 with a superimposed molecular ruler [divided into units of angstroms (Å)] and a cross-sectional view of the void volume (holes and crevices) possessed by the homolog.
Figure 3B:
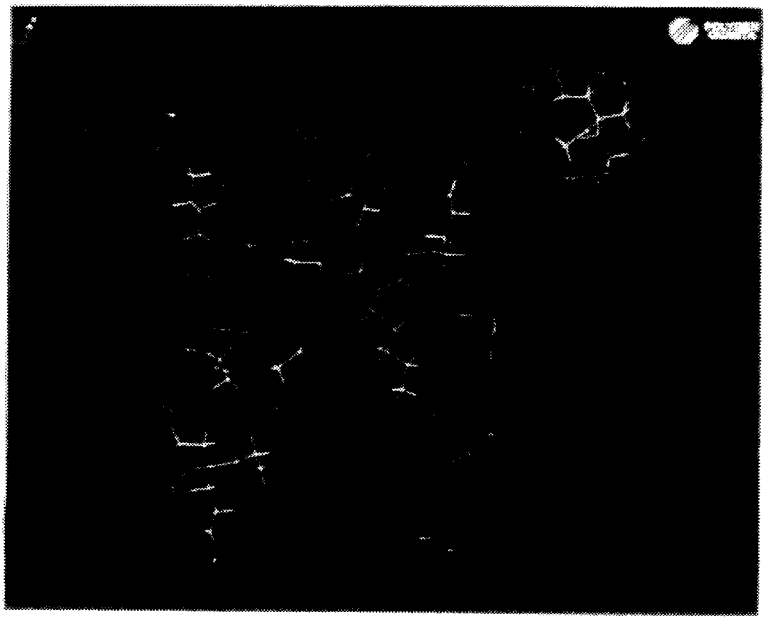

The third tier homolog of the unimolecular Micellanoic acid shown in FIG. 1, when viewed from an extended perspective with a depth gauge, reveals a significant void area and an extended radius very near to 40 Å, as shown in FIG. 3. The cross-sectional slice of the contracted conformer exposes holes and cavities within the molecular framework, also shown in FIG. 3.

It has been previously noted in the above-cited patent of the applicants that benzyl protected, unimolecular Micellynoic acids (Formulas 1 and 2) can be heterogeneously and catalytically reduced to afford the corresponding alkanols by Pd-C, ethanol, and tetrahydrofuran. The concomitant hydrogenation of the internal alkene moieties is straightforward under classical conditions, suggesting branch flexibility and the accessibility of internal functionality to facile chemical modification in accordance with the present invention. Since applicants have shown that there are no signs of "dense packing" at the surface, applicants have discovered accessible reactive sites capable of covalent and noncovalent attachment to guests. In accordance with the present invention, means are provided to manipulate these moieties within the spherical, symmetrical, dendritic macromolecules after construction. This allows for easy incorporation of internally located sensitive and/or reactive groups, which otherwise might be difficult to introduce or protect during cascade polymer construction.

Such reactive sites can be mono-, bi- and/or tridentate. Examples of monodentate reactive sites are olefins, amines, ethers, sulfides, phosphines, esters, amides, acids, pyridines, ketones, aldehydes, imines and halides. Examples of bidentate sites are acetylenes, pairs of amines, (diamines), pairs of ethers (polyethers), anhydrides, imides, pairs of ketones (diketones), pairs of pyridines (bipyridines), pairs of amides and esters, pairs of sulfides (disulfides), pairs of phosphines, pairs of halides, pairs of carbines, pairs of acetylenes (diynes), pairs of alkenes (dienes or olefins), thioethers, thioamines, thiophosphines, phosphinoamines, and phosphinoethers. An example of tridentate reactive sites is terpyridines.

The guests can be metallic or non-metallic ligands bound to at least one of the reactive sites. Examples of incorporated metals, generically known as metal complexes, are cobalt, platinum, copper, palladium, ruthenium, osmium, iron, rhodium, iridium, nickel, silver, and gold. As described below, such metals, if charged, can be bound and captured within void areas of the unimolecular micelles by covalent and/or H-bonding. The chemistry of the present invention allows for capture of such metal ions or clusters in a selective manner within various selected regions of these unimolecular micelies. Thus, hybrid or unimolecular Metallomicelles can be constructed wherein known amounts of various metals can be specifically incorporated into these unimolecular micellar systems to provide desired chemical characteristics to the final product.

For example, cobalt can be covalently bound within the void areas during expansion of the unimolecular micelle and then protected therein by contraction of the micelle, as discussed above. Such cobalt superclusters can be made wherein a single unimolecular micelle can contain a plurality of dicobalt centers, only limited by the number of reactive sites available within the dendritic arms proximate to accessible void regions. Uses of the cobalt superclusters include the mediation of specifically located carbon-carbon bond forming chemical reactions, known as Pauson-Khand reactions.[27] Similar dicobalt complexes are known to undergo reaction with other alkynes and alkenes.

Alternatively, nonmetals can also be incorporated into the unimolecular micelles to form non-metallic superclusters. Such nonmetals can be selected from the group including boron, aluminum, gallium, tin and zirconium. These include nonmetals, generally known as metalloids, which can be used for such applications as the formation of new carbon-carbon bonds.

It should be noted that boron is special in that it can form boron clusters via the propensity of boron atoms to form higher order species. An example of this is the cited (see Experimental Section) reaction of decaborane($B_{10}H_{14}$) with the alkene reactive sites.

More particularly, the preferred embodiment of the present invention provides a unimolecular micelle consisting essentially of a carbon core atom and essentially all alkyl arms extending therefrom as shown as Formula 2, wherein the R groups can indicate further branching in a quaternary manner. Each quaternary group defines at least four distinct void regions, each of the void regions being substantially lipophilic. As shown, at least one of the void regions includes at least one of the reactive sites, as shown in Formula 2, in the form of an alkene group. The molecules can include polyalkyne groups in void regions. By known chemistry, these alkene groups can be derivatized to various functionalities which are mono- bi- and/or tridentate as discussed above.

As discussed above, the outer surface of these unimolecular micelles can be made either lipophilic by the addition of uncharged functionalities on the surface of the micelle or can be hydrophilic by the incorporation of charged or more hydrophilic moieties. Such chemistry is well known in the art.[28]

Alternatively, the micelles can include a plurality of tiers defining the arms. Each of the tiers includes three branches extending therefrom a moiety bound to the next tier through peptide couplings. The discussion and examples below, discuss the synthesis of and provides examples of compounds including the peptide couplings. It should be noted that different couplings as well other chemical modifications to the branches or arms can effect the flexibility of the branches and arms and thereby, in combination with the nature of the terminal hydrodynamic reactive group on the arms or branches, can effect the extent to which the carboxyl expands and/or contracts. It should be further noted that although the terminal groups effect expansion and contraction dependant upon the nature of the environment, the arm or branch modification resulting in increased flexibility or rigidity of the arms affects the amount of contraction and expansion. For example, a unimolecular micelle with flexible alkyl branches will possess the ability to contract (or expand) more than a unimolecular micelle constructed with more rigid benzenoid arms, or arms containing sites of unsaturation (e.g. c=c or c c). Such incorporated rigidity can restrict expansion and contraction by limiting the "degrees of freedom", or number of ways, that a branch can fold and bend.

The present invention further provides a method of making cascade polymers, generally including the steps of forming a unimolecular micelle including internal void areas having reactive sites capable of covalent and hydrogen bonding to guests, and after construction of the micelle, bonding guests to a reactive site in a void area. The ligand is actually contained within the void area, the micelle thereby protecting the guest(s) from the surrounding environment. The amount of these polycomplexes bound within the micelles can be controlled, thereby forming metallo- and nonmetallo-clusters within the unimolecular micelle.

The method of construction of the unimolecular micelles is step-by-step which ultimately results in a fixed, controlled, predictable, and verifiable number of reactive sites (ligands) located at predetermined interior and exterior positions on the cascade polymer. Thus, the number and position of metal and nonmetal species (guests) capable of being incorporated inside, as well as outside, the macromolecular framework is also fixed, controllable, and predictable. Verification of attachment of guests to ligands is readily ascertained via standard spectroscopic techniques, particularly $^1$H and $^{13}$C NMR spectroscopies. The number of internally incorporated species is directly related to the size and number of dendritic arms containing predetermined reactive sites. Thus, a first tier, four-directional, unimolecular micelle with four precisely placed internal reactive sites will possess four incorporated species (metals or nonmetals) at precisely located positions. A second tier, four directional, unimolecular micelle with twelve predetermined reactive sites will contain 12 precisely attached guests after reaction, and so on. The relevant point is that the number of attached species is very controlled at specific loci based on our method of cascade construction. Examples are the hydrogenated, polyalcohol intermediates used in the preparation of the Unimolecular Micelles set forth in U.S. Pat. No. 5,154,853 to applicants and the Boron Superclusters and Cobaltomicellanes[29] described in the present application and exemplified below. Even if errors exist due to incomplete transformations giving use to less than pure bimolecular micelle structures, subsequent conversion to the corresponding Metallo- or Metalloid-micellane derivatives will have catalytic activity proportional to the number of internal metal centers.

Generally, the present invention provides a method of preparing a unimolecular micelle by forming a core atom having a plurality of flexible branching arms extending therefrom and terminating each arm with a hydrodynamic reactive group The terms "core atom" "flexible branching arms" and "hydrodynamic reactive group" are discussed above. What is critical, however, is that an unimolecular micelle can be prepared to function in terms of expansion and contraction in response to its environment by preparing the unimolecular micelle in accordance with the present invention.

More specifically, the general procedure (which is exemplified in detail in the examples closed) includes the steps of forming a first tier by amidating a tetra acid core with a branched amine moiety wherein termination of the branches are protected from the amidation under peptide coupling conditions. The termination of the branches then deprotected and then the first step is repeated to form additional tiers. Finally, the branches are terminated with the hydrodynamically reactive group.

The terminating step more specifically includes the steps of coupling an acid terminating branch with an acetate terminated monomer to provide acetic terminated branches and then, transesterifying the acetates to form alcohol terminations. Amine terminations are formed by coupling an acid terminated branch with a carbonate terminated monomer to provide carbonate terminated branches and then treating the carbonate with acid to form amine terminations. These synthetic approaches to the preparation of amine and alcohol terminations are exemplified in detail in the experimental section below.

The method of preparing the micelle can further include the step of modifying the flexibility of the branches or arms to modify the extent to which the arms will extend. For example, the incorporation of olefinic, or unsaturated moieties, such as a cis substituted carbon-carbon double bond will decrease branch chain flexibility due to restricted rotation about the (>c=c<) carbon-carbon double bond; represented by the formula

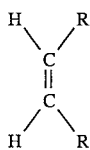

as wherein R=any substituent group (i.e., alkyl) but not hydrogen. This is opposed to a 'trans' substituted double bond represented by

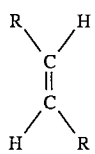

Isomerization does not occur under normal conditions:

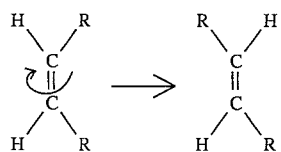

'Cis' to 'trans' isomerization usually only occurs as a result of some external stimulus such as heat and light.

The placement of such a group into the branch(es) of a unimolecular micelle physically puts a 'molecular kink' into the said branch; thus the arm(s) with these sites of unsaturation will not be able to extend as far as they would if they had no cis double bond. If any tier of the unimolecular micelle possess at least one carbon-carbon double bond per attached monomers, then the surface of the unimolecular micelle can not physical exteracl as far away from the center of the unimolecular micelle than it would if it did not possess any double bonds.

Carbon-carbon double bonds can be introduced via a number of methods that are well known in the art. Once such method combines monomer connectivity with carbon-carbon double bond incorporation. This is known as a Wittig Reaction whereby the coupling of a phosphoniumylide with a carboxyl group, such as an aldehyde, produces a carbon-carbon double bond.

The idea of incorporating "molecular kinks" into branch chains can be extended to include other groups with similar geometries, such as complexed bipyridines

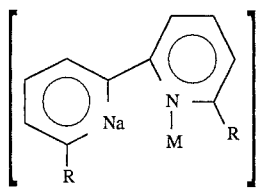

and phenanthrenes,

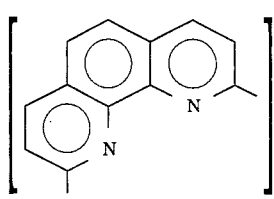

or something as simple as a disubstituted benzene

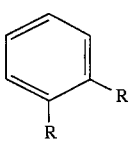

While the inclusion of these types of groups in cascade superstructures inhibits expansion rigidity also reduces the extent of contraction due to the loss of conformational degrees of freedom. The more degrees of freedom that a chain, or branch, has then the more conformations, it can obtain and hence the more compact it will be able to become. The less 'degrees of freedom' that a branch has then the fewer conformations it can adopt and hence, it will not be able to become as compact as a chain of an equal number of carbons with no 'kinks'.

As discussed above, the unimolecular micelle can be expanded to allow access of metal and non-metal guests or the reactive sites, thereby providing a means of access to the complex center(s) within the void area after construction of the micelle. Upon attaining access to the catalytic site(s),[5] the transient guest(s) is (are) bound to the reactive site and the micelles contracted to contain and protect the transient guest(s). As discussed above, such expansion providing accessibility to one or more of these catalytic sites can be achieved by altering the environment, such as by changing the pH[25] of the external environment solvent or medium. Additionally, these unimolecular micelles having a surface which is more soluble in lipophilic solvents can be transferred to a common organic solvent, such as $CH_2Cl_2$, $CHCl_3$, $C_6H_6$, thereby expanding these lipophilic micelles allowing accessibility. The micelles then are returned to a more hydrophilic solvent causing contraction, due to an inability of the solvent to solvate the surface.[30] This has been demonstrated on classical polymers with organic solvents such as tetrahydrofuran, which causes polymer swelling.

In view of the above, the present invention provides a method of manipulating the unimolecular micelles in an environment by reversibly changing the solubility of the outer surface of the micelle in the environment while reversibly extending the arms of the micelle to expand and contract the micelle. Generally, this can be done by changing the environment to increase the solubility of the outer surface of the micelle in that environment. Specifically, as discussed above, this can be done by either changing the pH of the environment or the hydrolipophilic properties of the environment or other properties known in the art. Thusly, the present invention provides a method for reversibly changing the hydrodynamic radius of the micelle.

By changing the hydrodynamic radius of the micelle, the present invention provides for uses not necessarily related to inclusioning of guests in void areas of the micelle. For example, the experimental evidence below demonstrates that the micelles made in accordance with the present invention can be expanded to precisely known outer radii. Thusly, the present invention can be utilized as size standards for various molecular (i.e. sieving, chromatographic separations standardizing) and the like processes. The sizing functionality of the micelles also allow for precise engineering for a particular environment of the size of the micelles to allow for passage or filtration of the micelles as desired. This can be useful in industrial applications as well as biological applications.

The ability of the present invention to expand and contract in combination with the ability of the unimolecular micelles inclusion of various guest(s), such as metals, drugs, or the like, and then expand in a certain environment to release the guest(s) provides a great utility for the present invention. The micelles can be engineered so as to expand in a particular environment, whether it be a basic environment, or an acidic environment, a hydrophilic environment, etc., so as to be loaded with a guest in that environment. The micelles can then be removed from the environment, thereby trapping the guest therein, as described above and demonstrated in the example section below. This can be designed with a target in mind wherein the target has a local environment which would also caused expansion of micelies. In other words, if the micelles expand in an acidic environment and a target is surrounded by a pH neutral environment or a basic environment wherein the micelles remain contracted (thereby containing the guest) when the micelles reach the target having the acidic environment, the micelles will release the guest at the environment. Hence, the unimolecular micelles made in accordance with the present invention can be used a carrier to carry a guest through a system and release the guest at the target having the known local environment. This method of guest delivery can have industrial as well as biological applications. The data presented in the example section demonstrate this utility by showing that guest(s) can be included and released and further show that unimolecular micelles can be engineered to expand, include guest(s), and contract in various environments depending upon the terminal moieties on the arms or branches of the micelies.

The target for release of the guest molecules for the unimolecular micelles may be located in a circulating system wherein the micelles may have a single pass by or through the target or multiple passes through the circulating system. If the micelles are sized to remain in the circulating system for more than one pass, then the micelles can be delivered to the circulating system and release the guest molecules from the micelles at the target each time the micelles circulate into the hydrodynamic environment of the target. Thusly, in an industrial device, where a certain component of the device may be in a hydrodynamic environment different from the remainder of the circulating system, the micelles can be used to include guest molecules to be delivered to the target site wherein the micelles maintain there contracted state thereby containing the guest molecules throughout the circulating system. If the target site has a hydrodynamic environment in which the micelles will expand and the release the guest molecules, the micelles will be delivered to the target site by the circulating system and release at least some of the guest molecules at the target site. As the micelles are moved from the target site by the circulating system, they will continue to contain the remainder of the guest molecules until the circulating system returns the micelles back to the target site for more or continued release. Thusly, the unimolecular micelles of the present invention can be used as a delivery system in a circulating system for continued targeted release of guest molecules at a specific site. Thusly, molecules such as lubricants, disenfectants, or the like or active molecules such as catalysts or the like can be delivered to specific sites.

The unimolecular micelles of the present invention can include arms having alkene moieties. The alkene moieties can be treated with a metallocarbonyl in an aprotic solvent, the metallo addition being complexed to the internal ligand site(s).

More specifically, the metallo moiety can be selected from the group including, but not limited to, cobalt, platinum, copper, palladium, ruthenium, osmium, iron, rhodium, iridium, nickel, silver, and gold.

The aprotic solvent can be selected from, but is not limited to, the group including $CH_2Cl_{12}$, $HCCl_3$, $CCl_4$, R—O—R' wherein R and R' are selected from the group consisting of aralkyl and aryl groups, $C_6H_6$ and $CH_3C_6H_5$.

The unimolecular micelles of the present invention can also include polyalkyne moieties. These polyalkyne moieties can have bonded thereto a zero-valent metal under reductive conditions and in the presence of a phosphine donor to the alkene moieties. The phosphine is thermolysed to generate the zero-valent metal trapped within the void area of the unimolecular micelle.

A further alternative is for the micelle to include arms having bidentate diamino chelate ligands. To produce these compounds, the bonding step discussed above consists of chelating divalent copper to the ligand. Specifically, the bidentate is formed by alkylating a chloro-terminated monomer of the formula:

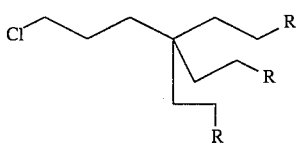

wherein R=CH$_2$OR', CO$_2$R", CN and CH$_2$NR$_2$'", R'=Me, CH$_2$C$_6$H$_5$; (R"=Me, Et, Dr, bu(t), CH$_2$Aryl and R'"=H, alkyl, aryl, and alkynyl with (2,3, or 4-lithiomethyl-2'3' or 4'-methyl) bipyridine to form the bidentate diamino of the formula selected from the group consisting of:

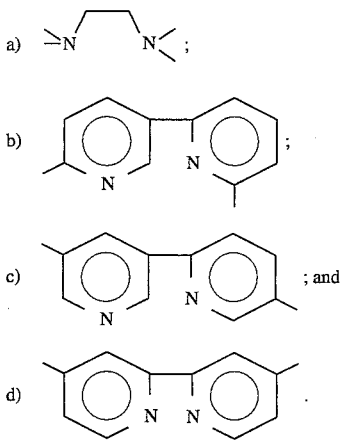

These steps can be followed by the subsequent steps of the lithiating of terminal methyl groups and adding further polyhalides to form further internal bi- or tridentate loci in void areas of the unimolecular micelle.

A further alternative is wherein the unimolecular micelle includes arms having polyalkyne moieties, the bonding step discussed above being further defined as treating the alkene moiety with a acetonitrile activated decarborane moiety.

In accordance with the above methods, bidentate diamino chelate ligand of the formula:

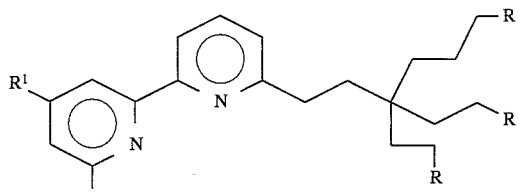

can be made wherein R=H, alkyl, or CH$_2$OR'" where R'"= CH$_3$, CH$_2$C$_6$H$_5$ and R'=CO$_2$R", CH$_2$OH, CH$_2$NH$_2$, CN or CH$_2$X wherein X is a halogen, OMs (OSO$_2$CH$_3$) or OTs (OSO$_2$C$_6$H$_4$CH$_3$).

The following examples demonstrate the ability of the present invention to provide incorporation into unimolecular micelles of metal and nonmetal centers.

EXAMPLE SECTION

A. Complexes With Cobalt
General Procedure for the Preparation of Cobalt-based Metallomicellanes.
12-Cascade:methane[4]:(5,6-hexacarbonyldicobalt)nonylidyne:(2-oxapentyl)benzene.
[First generation Cobaltomicellane]

A solution of CH$_2$Cl$_2$ (10 mL), tetraalkyne-dodecabenzyl ether {12 Cascade:methane[4]:(5,6-yn)nonylidyne:(2-oxapentyl)benzene (0.5 g) and octacarbonyldicobalt (0.30 g, 0.89 mmol) was stirred for 12 hours under a N$_2$ atmosphere at 0° C. The solvent was removed in vacuo and the residue was subjected to non-aqueous reverse phase chromatography (C$_6$H$_6$) to afford (88%) the octacobaltdodecabenzyl ether as a viscous red oil:

$^{13}$C NMR δ22.8 (CH$_2$CH$_2$O), 25.6 [Co$_2$(CO)$_6$C$_2$CH$_2$CH$_2$], 32.6 (C$_2$CH$_2$CH$_2$O), 34.0 [Co$_2$(CO)$_6$C$_2$CH$_2$], 36.4 [C$_{4°}$, Co$_2$(CO)$_6$C$_2$CH$_2$CH$_2$CH$_2$], 71.2 (CH$_2$OCH$_2$C$_6$H$_5$), 72.8 (OCH$_2$C$_6$H$_5$), 127.3, 127.4, 128.3, 138.6 (C$_6$H$_5$), 201.0 (CO); $^1$H NMR δ0.60–2.70 [br m, (CH$_2$)$_3$Co$_2$(CO)$_6$C$_2$(CH$_2$)$_3$C{CH$_2$CH$_2$}$_3$, 96H], 3.40 (br s, CH$_2$OCH$_2$C$_6$H$_5$, 24H), 4.46 (br s, CH$_2$C$_6$H$_5$, 24H), 7.30 (br s, C$_6$H$_5$, 60H); IR (neat) v=3075, 2940, 2870, 2085, 2044, 2015, 1280, 1100, 745 cm$^{-1}$ 36-Cascade:methane[4]:nonylidyne:(5,6-hexacarbonyldicobalt)nonylidyne:(2-oxapyntyl)benzene.
[Second generation Cobaltomicellane]

$^{13}$C NMR δ22.8 (CH$_2$CH$_2$O), 23.5 [CH$_2$(CH$_2$)$_4$CH$_2$]29.7 [(CH$_2$)$_3$CH$_2$CH$_2$ (CH$_2$)$_3$], 25.7 [Co$_2$(CO)$_6$C$_2$CH$_2$CH$_2$], 32.6 (CH$_2$CH$_2$CH$_2$O), 34.0 [Co$_2$(CO)$_6$C$_2$CH$_2$], 36,4 [C$_{4°}$, Co$_2$(CO)$_6$C$_2$CH$_2$CH$_2$CH$_2$], 36.7 [CH$_2$(CH$_2$)$_6$CH$_2$] 71.2 (CH$_2$OCH$_2$C$_6$H$_5$), 72.8 (OCH$_2$C$_6$H$_5$), 127.3, 127.4, 128.3 138.6 (C$_6$H$_5$), 202.0 (CO); $^1$H NMR δ0.60–2.70 [br m, (CH$_2$)$_8$, (CH$_2$)$_3$Co$_2$(CO)$_6$C$_2$(CH$_2$)$_3$C{CH$_2$CH$_2$}$_3$, 356H], 3.42 (br s, CH$_2$OCH$_2$C$_6$H$_5$ 72H), 4.46 (br s, CH$_2$C$_6$H$_5$, 72H), 7.30 (br s, C$_6$H$_5$, 180H); IR (neat) v=3075, 2940, 2870, 2085, 2044, 2015, 1280, 1100, 745 cm$^{-1}$ The reactivity within the lipophilic core of these unimolecular micelles was conducted via treatment of the internal alkene moieties of Formulas 1 and 2 with Co$_2$(CO)$_8$ [31] in an aprotic solvent such as CH$_2$Cl$_2$, shown in FIG. 4. Dicobaltoctacarbonyl is well known to form additional complexes to acetylenes and has been successfully employed for their protection.[31] These resultant dicobalt complexed alkynes act not only as protecting groups but also promote ene-yne cyclopentenone cyclization,[32] thus affording entry to a novel series of carbocyclic substituted micelles via chemical modification of their internal lipophilic region. Substituents attached to the guest alkene allow precise placement of diverse functionality within one or more of the micellar void volume regions.

Figure 4C:
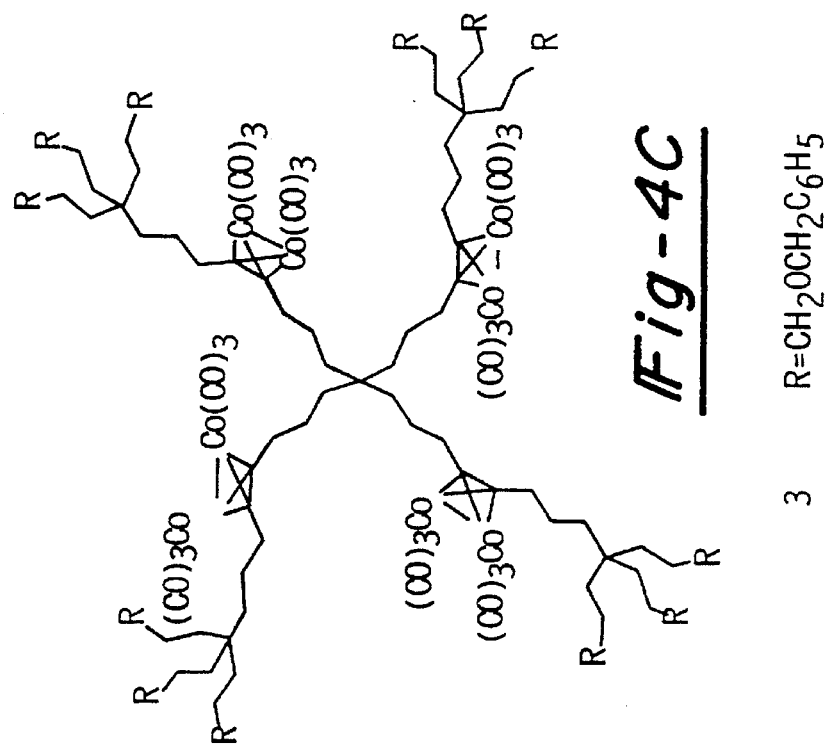
FIG. 4 shows the preparation of the first tier of a unimolecular Cobaltomicelle and its reaction with olefins.
Figure 4A:
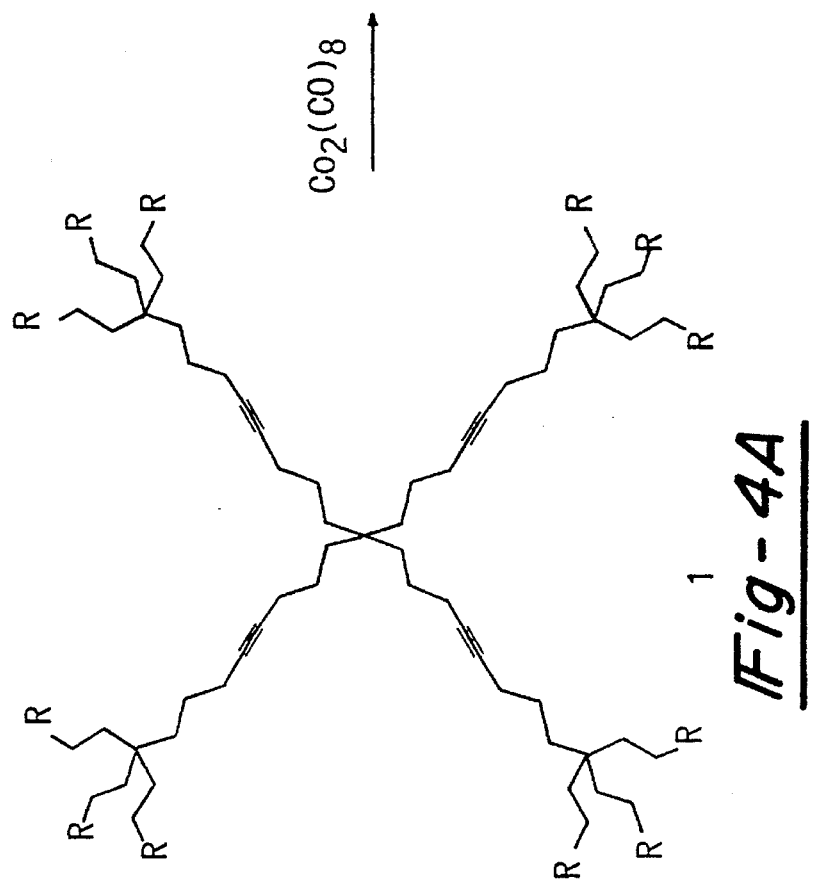

The information of functionalized terminal alkene guests is envisioned via the formal 2+2+1 cyclization. Thus, treatment of cobalt superclusters Formulas 3 or 4 (FIG. 4) with 4-vinylpyridine or methyl acrylate should afford Formulas 5a,b or 7a,b (FIG. 4). Benefits of the transformation include the incorporation of α,β-unsaturated carbonyl moieties and precisely anchored reagents which can be used to ascertain an accurate "depth of reagent" inside the inherent cavities in these derivatized unimolecular micelies. Insight also is afforded into the regiochemistry of the cyclizations.[34a,35] The nature of the reagents environment (i.e., hydrophobicity, lipophilicity, mobility, density, etc.) can then be related to that observed for classical micelies.[2]

Isolation and purification of the Co$_2$(CO)$_6$ intermediates have been reported[32] generally not to be required prior to ene-yne cyclization due to high conversions. Treatment of the tetraalkyne Micellane (Formula 1) with dicobaltoctacarbonyl affords (≈100%) the deep red, viscous dicobalthexacarbonyl adduct (Formula 3). Formation was evidenced by the appearance of $^{13}$C NMR resonances at 200.3 (C≡O) and 99.6 ppm [C$_2$(Co$_2$(CO)$_6$], as well as the disappearance of signals at 80.1 and 19.3 ppm attributed to the C≡C and α-CH$_2$ precursor moieties, respectively. Further support was provided by the symmetry of the $^{13}$C NMR spectrum and severe broadening of the $^1$H NMR spectrum, and an IR absorption at 2000 cm$^{-1}$.

4-Dicobalt clusters were attached at four discrete loci at a distance no greater than 6.4 Å[36] from the core atom. Similar $^1$H and $^{13}$C NMR spectral signals are observed when the dodecaalkyne derivatized Micellane (Formula 2) is treated with Co$_2$(CO)$_8$ to afford the dodecadicobalt supercluster (Formula 4). As each tier is added, the number of internal alkene sites increases (4→12→36→108 . . . ), thus placing each set of alkene centers at a discrete distance from the core (6.4, 17.3, 28.4, and 37.4 Å, respectively); each center available for subsequent complex formation. Since the dicobalt clusters are protecting groups for the alkene moiety, the initial 4 clusters at 6.4 Å were maintained during construction of the next tier. Addition of twelve equivalents of Co$_2$(CO)$_8$ will afford a micellar species with 16-dicobalt clusters. This procedure can be repeated with added tiers affording 52 (4+12+36)- or 160 (4+12+36+108)dicobalt cluster centers within the hydrophilic surface coat.

One is not limited to a single metal source. Each tier can incorporate different metal ions or clusters. Thus, the initial 4-dicobalt clusters at tier 1 can be covered by 12-Pt(0) (next section) sites at tier two. Since each tier is constructed independently of the preceding layer, numerous possibilities are conceivable and attainable, provided the chemical stability is maintained during the attachment of subsequent tiers.

B. Complexes with Platinum

The incorporation of moieties into dendritic "void regions" includes the incorporation of zero-valent metals, such as Pt(0).[37] Thus, the utilization of Pt(0), generated from K$_2$PtCl$_4$ under reductive conditions (NaBH$_4$,EtOH) in the presence of R$_3$P (R=alkyl, aryl or aralkyl) leads to platinacycles (Formulas 7 or 8), depending on the size and number of unsaturated centers, as noted above, of the unimolecular micelle (FIG. 5). As the tiers are added, the cavities are eventually sealed (onset of dense packing). However, they are still porous due to the facile molecular motion of the surface functionality at ambient and above temperatures. Thus, thermolysis of the platinocycles within the metallospheres liberates irreversibly the volatile R$_3$P ligands to generate Pt(0)[37] metal atoms trapped within the inner lipophilic microenvironment.

Examination of these Metallomicelles can be expanded to include the preparation of poly-Pd(0) adducts. Although these palladiocycles are less stable towards external parameters, such as oxidation and heat, they exhibit chemistry similar to their platinum counterparts.[31]

The generation and migration of metal(0) species within inert hydrocarbon pockets afford small, e.g. Pt(0)$_{n'}$, clusters. The mobility within a single pocket affords at least four similar Pt(0)$_n$ cluster centers, but if interregion migration occurs, a "colloidal transition metal cluster"[38] is possible. Other platinum family metals can be incorporated via similar technology.[38] If intracavity migration occurs, the cluster is limited to a fixed number of metal atoms, and each cluster and symmetry is retained; whereas, if intercavity metal atom migration occurs, cluster size is variable and molecular dissymmetry of the metallomicelle results.

C. Complexes with Copper

Copper-based "metallomicelles" have been shown by Menger to significantly enhance the rate of phosphodiester hydrolysis [e.g., nerve agent GD; (RO)$_2$POF]by as much as 10$^6$ due to increased electrophilicity created by constrained metal centers.[2] Introduction into the cascade of a suitable Cu$^{2+}$ligand leads to copper-based metallospheres that possess this capability.

Figure 6A:
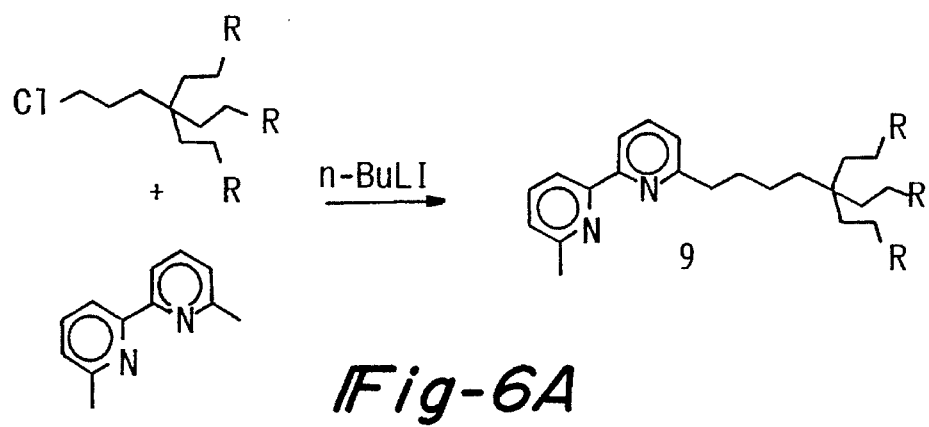
FIG. 6 shows the synthesis of a representative copper-based unimolecular Metallomicelle.
Figure 6B:
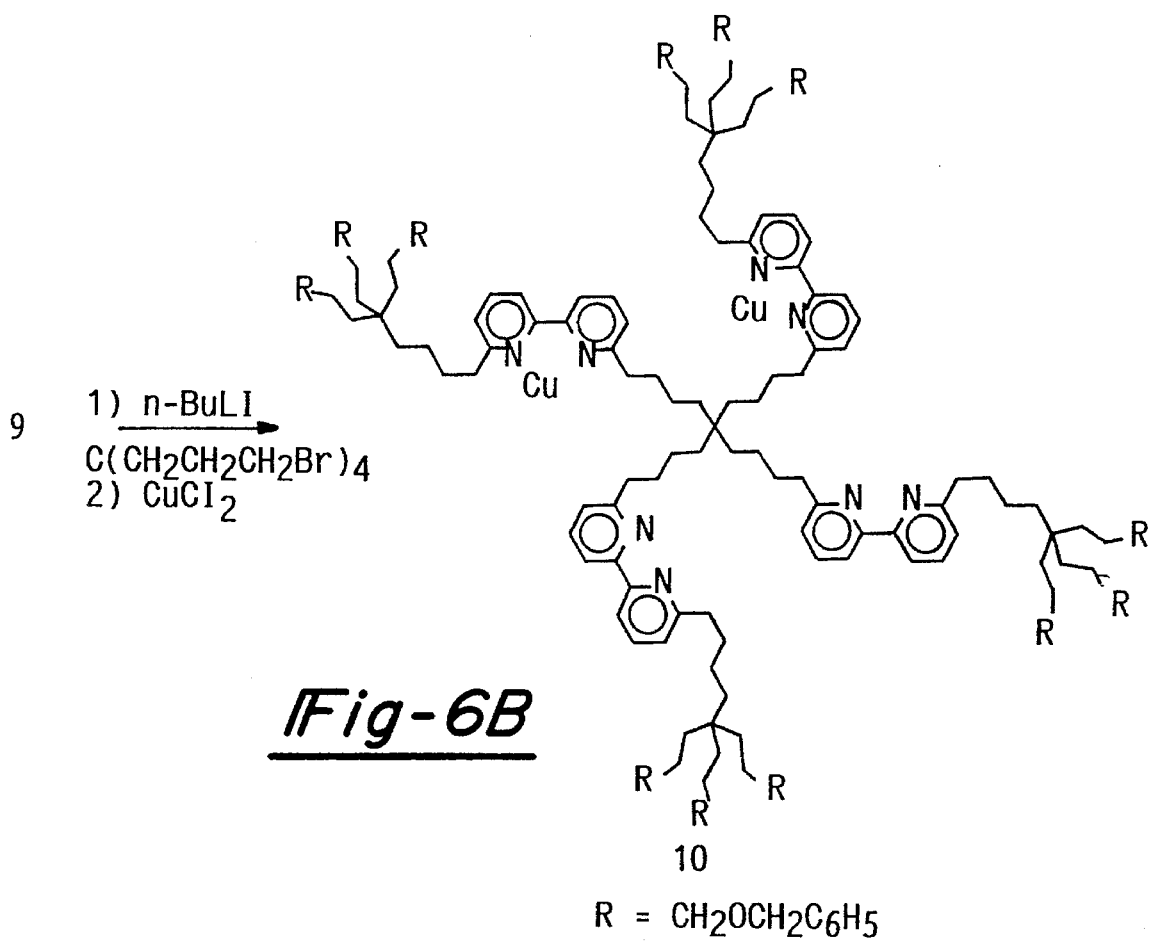

Copper-based metallomicelles are constructed from novel cascade building blocks that incorporate bidentate diamino ligands. Alkylation of the chloro-terminated monomer [4-(3-chloropropyl)-4-(3-benzyloxypropyl)-1,7-dibenzyloxyheptane][5] with (2-lithiomethyl-2'-methyl)bipyridine[39] easily affords a rigid building block (Formula 10) with the requisite chelate site. Since selective metallation has been demonstrated,[40,41,42] subsequent lithiation of the remaining terminal methyl group and addition of a poly-halide core[5] (e.g., 4, 12, or 36 terminal halides, etc.) provides a series of cascade infrastructures (Formula 11) possessing these internal bidentate loci (FIG. 6). Although copper inclusion is shown, this technique can be applied to many other metal ions.[43]

D. Boron Clusters

General Procedure for the Preparation of Boron Superclusters.

12-Cascade:methane[4]:5,6-(1,2-dicarba-closododecarborane)nonylidyne:(2-oxapentyl)benzene.

[First generation boron supercluster]

A solution of acetonitrile (1.0 mL) and excess decaborane (0.3 g, 2.4 mmol) was stirred at 25° C. under a N$_2$ atmosphere, for 30 min. Subsequently, a mixture of toluene (7.0 mL) and the tetraalkyne-dodecabenzyl ether {12-Cascade:methane[4]:(5,6-yn)nonylidyne:(2-oxapentyl)benzene}(0.5 g, 0.22 mmol) was added. After refluxing for 24 hours, MeOH (5.0 mL) and 10% HCl (1.5 mL) were added and reflux was continued for another 12 hours. Upon cooling to 25° C., the solvent was removed in vacuo, CH$_2$Cl$_2$ (50 mL) was added and subsequently washed with 10% Na$_2$CO$_3$ (2×50mL) and saturated brine (2×50 mL), and dried (NaSO$_4$). Concentration in vacuo followed by non-aqueous reverse phase chromatography (10:0.1 v/v C$_6$H$_6$: EtOAc) afforded (92%) the pure tetra-1,2-dicarba-closododecarborane supercluster: $^{13}$C NMR δ23.5 (B$_{10}$H$_{10}$C$_2$$\underline{C}$H$_2$$\underline{C}$H$_2$ $\underline{C}$H$_2$CH$_2$O), 29.6 (B$_{10}$H$_{10}$C$_2$$\underline{C}$H$_2$), 32.4 ($\underline{C}$H$_2$CH$_2$CH$_2$O), 36.5 ($\underline{C}$$_{4°}$,B$_{10}$H$_{10}$C$_2$CH$_2$CH$_2$$\underline{C}$H$_2$), 71.2 ($\underline{C}$H$_2$O), 72.8 (O$\underline{C}$H$_2$C$_6$H$_5$), 127.3, 127.4, 128.3, 138.6 ($\underline{C}$$_6$H$_5$); $^1$H NMR δ0.85–2.10 [m, (CH$_2$)$_3$B$_{10}$$\underline{H}$$_{10}$C$_2$(CH$_2$)$_3$C{$\underline{C}$H$_2$CH$_2$}$_3$, 136H], 3.40 (br s, C$\underline{H}$$_2$O, 26H), 4.46 (br s, OC$\underline{H}$$_2$C$_6$H$_5$, 24H), 7.30 (br s, C$_6$$\underline{H}$$_5$ 60H); $^{11}$B NMR ($^1$H decoupled) δ-19.6(s, $\underline{B}$$_{3,6}$), 0.5 (m, $\underline{B}$$_{4, 5, 7,11}$), 23.6 (s, B$_{8, 10}$), 35.6 (br s, B$_{9,12}$); $^{11}$B NMR ($^1$H coupled) δ-19.6 (d, $\underline{B}$$_{3,6}$, J=145.2 Hz), 0.5 (m, $\underline{B}$$_{4,5,7,11}$), 23.6 (d, B$_{8,10}$, J=119.5 Hz), 35.6 (br s, $\underline{B}$$_{9,12}$); IR (neat) v 3080, 3030, 2920, 2860, 2575, 1100, 745, 700 cm$^{-1}$.

36-Cascade:methane[4]:nonylidyne:5,6-(1,2-dicarba-closododecarborane)nonylidyne:(2-oxapyntyl)benene.

[Second generation boron supercluster]

The experimental procedure is the same as that described for the first generation, 12-Cascade, boron supercluster. $^{13}$C NMR δ22.5 [C(CH$_2$$\underline{C}$H$_2$)$_4$$^{int}$], 23.5[C(CH$_2$CH$_2$)]$_4$$^{ext}$, $\underline{C}$H$_2$CH$_2$O, 29.0 [C($\underline{C}$H$_2$CH$_2$CH$_2$CH$_2$)$_4$$^{int}$], 29.5 (B$_{10}$H$_{10}$C$_2$ $\underline{C}$H$_2$), 31.5 [C(CH$_2$$\underline{C}$H$_2$CH$_2$)$_4$$^{int}$], 32.6 ($\underline{C}$H$_2$CH$_2$CH$_2$O), 36.6 [m, $\underline{C}$$_{4°}$, $\underline{C}$$_{4°}$($\underline{C}$H$_2$)$_4$], 71.3 ($\underline{C}$H$_2$O), 72.8 (O$\underline{C}$H$_2$C$_6$H$_5$), 127.3, 127.4, 128.3, 138.6 ($\underline{C}$$_6$H$_5$); $^1$H NMR δ0.70–2.15 [br s, (C$\underline{H}$$_2$)$_8$$^{int}$ (C$\underline{H}$$_2$)$_3$B$_{10}$H$_{10}$C$_2$(CH$_2$)$_3$C{C$\underline{H}$$_2$C$\underline{H}$$_2$}$_3$$^{ext}$, 372H], 3.41 (br s, C$\underline{H}$$_2$O, 72H), 4.47 (br s, OC$\underline{H}$$_2$C$_6$H$_5$, 70H), 7.30 (br s, C$_6$$\underline{H}$$_5$; 180H); $^{11}$B NMR ($^1$H decoupled) δ—19.6 (s, $\underline{B}$$_{3,}$6), 0.5(m,$\underline{B}$$_{4,5,7,11}$), 23.6(s, $\underline{B}$$_{8,10}$), 35.6 (br s, $\underline{B}$$_{9,12}$); IR(neat) v=3080, 3030, 2920, 2860, 2575, 1100, 745, 700 cm$^{-1}$ Synthesis of water-soluble boron clusters to be used in cancer treatment, specifically, boron neutron capture therapy, has been the subject of recent investigations.[44]Localization of high concentrations of boron, provided by 1,2-dicarba-closo-dodecarboranes (o-carboranes), at tumor sites and subsequent neutron activation results in the decay of $^{10}B$ (20% natural abundance) to an α-particle and $^7Li$ which interferes with cancer cell replication. Aqueous solubilization has thus far relied on transformation of $B_{10}H_{10}$ closo-structures to ionic $[B_9H_{10}]^-$ nido-structure,[44a,b] or attachment of a single o-closo-carborane to a small, water-soluble delivery molecule.[44c] These methods lack the advantage of delivery of a maximum amount of boron with a minimum dose. Water-soluble polycarborane cascades would circumvent this limitation.

Figure 7A:
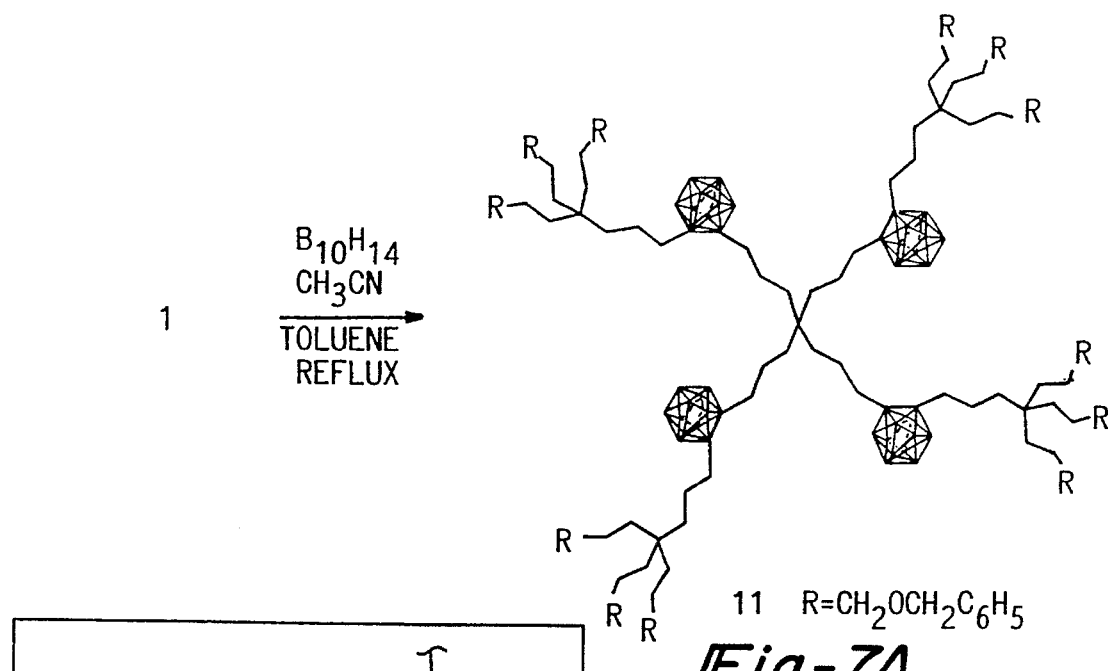
FIG. 7 shows the preparation of the first and second tier unimolecular Carboranomicelles possessing four and twelve internal ortho-carborane moieties, respectively.
Figure 7B:
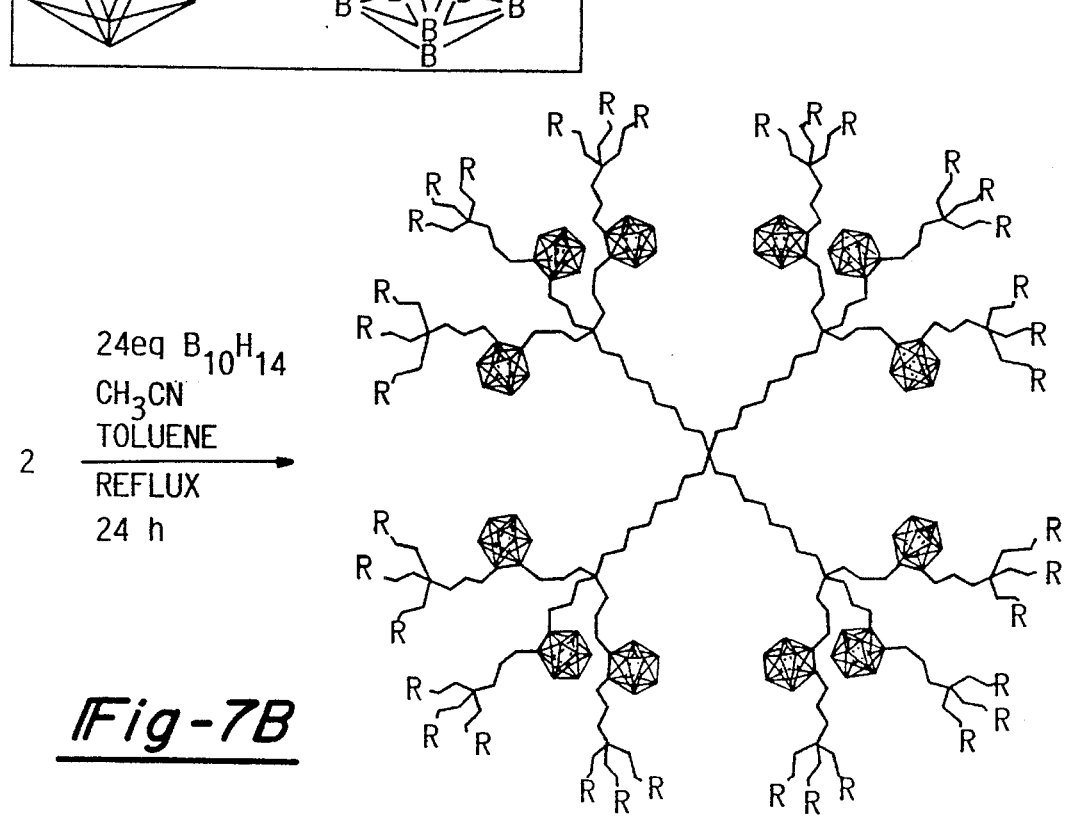

Initial investigations of cascade-based, boron superclusters have focused on the successful synthesis of the tetrakis(o-carborane)[45] (Formula 11) via treatment of the polyalkyne monomer Formula 1 (FIG. 7) with acetonitrile activated decaborane. Similarly, treatment of the dodecaalkyne cascade (Formula 2) with decaborane yielded the dodeca-o-carborane (Formula 12). Evidence for the formation of Formulas 11 and 12 included the disappearance of $^{13}C$ NMR peaks at 80.1 (C≡C) and 19.3 ppm (CH$_2$C≡C) and the appearance of a peak at 29.5 ppm (CH$_2$C$_2$B$_{10}$H$_{10}$). The $^1H$ NMR spectrum exhibited a sharp, intense peak at 2.51 ppm (B$_{10}$H$_{10}$) postulated to arise by the rapid rate of quadruple relaxation in boron.[46] The exceptional stability of carboranes is employed to obtain supercluster water-solubility. Thus, hydrogenolysis of the benzyl ether moieties (Pd-C) followed by oxidation of the terminal alcohols (CrO$_3$·H$_2$SO$_4$) to carboxylic acid groups affords the requisite solubilizing terminal moieties after treatment with base. Third and fourth tier cascade intermediates, when subjected to the same procedures, would afford water-soluble superclusters possessing 36 and 108 o-carborane clusters, respectively.

Figure 8A:
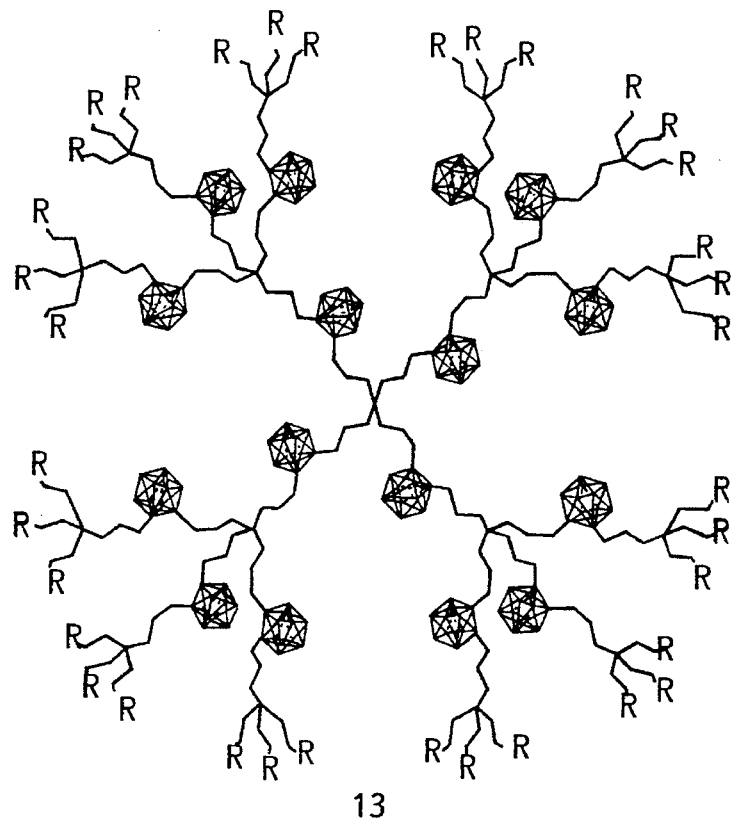
FIG. 8 shows the layering of tiers of the unimolecular Carboranomicelle possessing greater than four internal carborane units; and illustrating the ease of preparation of combinations of multiple (non)metallo sites feasible by the noted tier construction methodology of these unimolecular micelies.
Figure 8B:
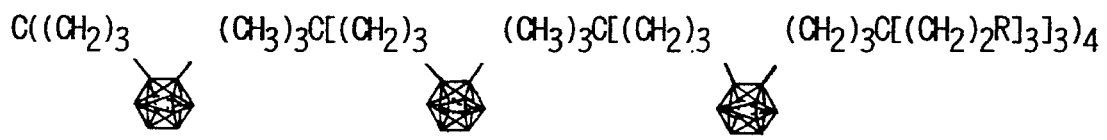

Alternatively, carborane superclusters are prepared wherein each tier or layer of monomer added is treated with decaborane to provide a maximum amount of o-carborane groups within the internal Micellane environment. Thus, second and third generation cascades (Formulas 13 and 14) possess 16 and 52 o-carborane moieties, respectively (FIG. 8).

E. Characterization

Proof of structure is ascertained by NMR spectroscopy.[5] The inclusion of these anisotropic centers within the lyophilic core facilitates NMR studies of included guest(s) moieties and their immediate environment. These data afford insight to the degree of inclusion (penetration) within spherical (Hartley model) micelies. Electron microscopy is used to visually demonstrate the size and shape of the product(s). Since these spherical medio/macromolecules swell and contract under varying solvent and pH conditions,[25] controlled access to these inner metal loci is achieved under very rigid conditions. The introduction of appropriate guests to these potentially catalytic sites is realized in an aqueous environment, since non-porotic guests favor these lipophilic inner regions. The synthesis, characterization, and chemistry of water-soluble unimolecular metallomicelles and metalloidomicelles possessing inner lipophilic pockets containing metal catalytic sites are herein disclosed.

The above examples demonstrate the ability of the present invention to fill void regions by chemical means within dendritic macromolecules. As additional layers are added, constraint will then be imposed at the onset of surface "dense packing" in these dendritic systems. The chemistry of the present invention utilizes inter- and intra-molecular host-guest interactions, as well as chemical transformations at a pre-determined depth within the specific micellar environment. Accordingly, the present invention provides means of utilizing not only the exterior of the micelle for interaction with this environment, but also the lipophilic interior of the unimolecular micelle. These modifications allow for reaction of the micelles in a dramatic fashion with the surrounding environment. The surrounding environment, physiologically, can be drastically modified by such an interrelationship. Such modification can be medicinal in nature, the micelles providing a pharmacological delivery mechanism.

F. Demonstration of pH Dependence of Hydrodynamic Ratio of Micelies

The following examples demonstrate the synthesis of unimolecular micelles having flexible branching arms and terminating each arm with a hydrodynamic reactive group, such as amine or alcohol. The data demonstrate a pronounced pH dependence. Accordingly, the following experiments demonstrate the method of synthesis of the inventive micelles as well as the expansion characteristics in changing environments.

G. Synthetic Aspects

Figure 9:
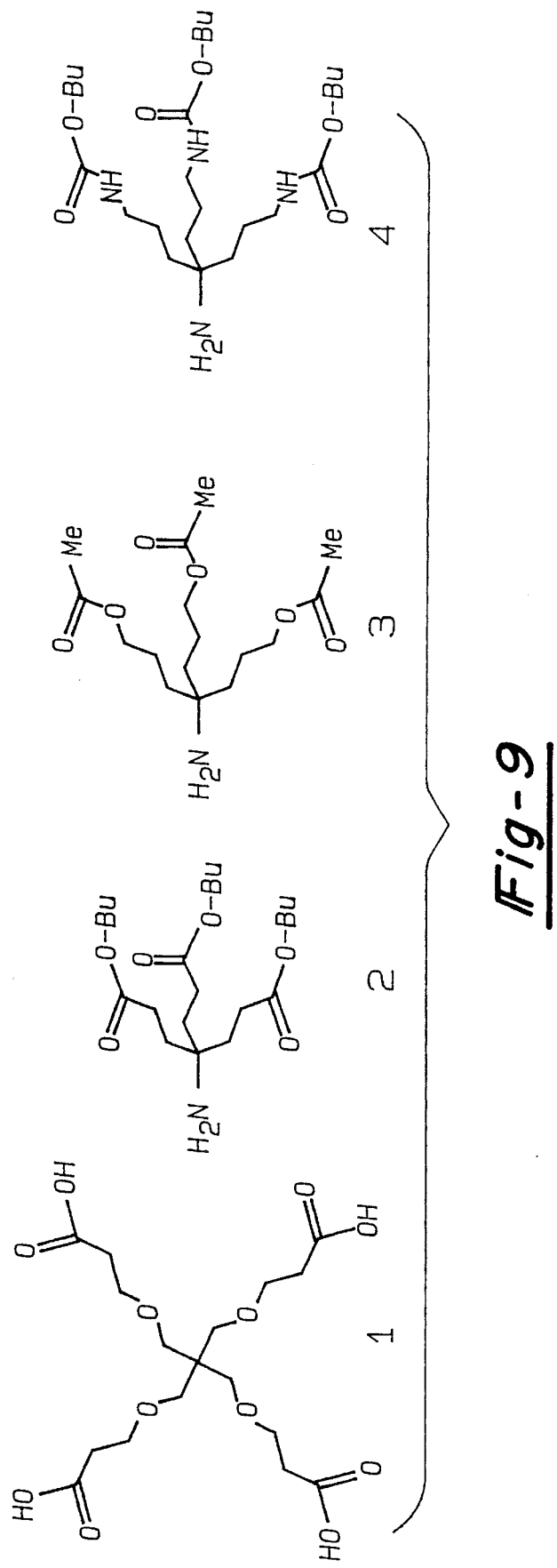
FIG. 9 shows building block "modules" for cascade synthesis of micelles made in accordance with the present.
Figure 10:
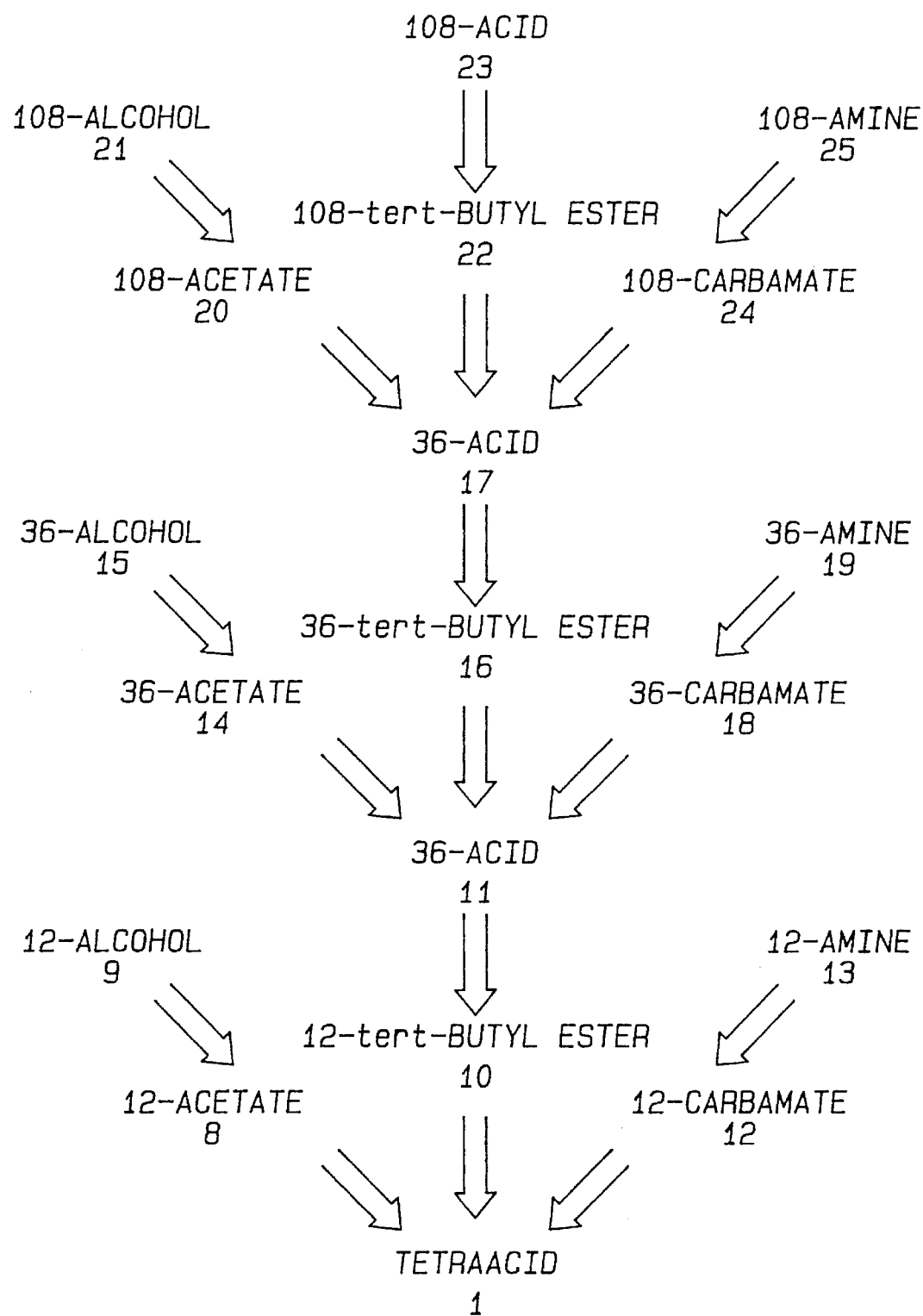
FIG. 10 shows the retrosynthetic "tree" illustrating the derivation of alcohol, acid and amine terminated cascade polymers (micelies) made in accordance with the present invention.

As shown in FIG. 9, while tetraacid 1 and amines 2 and 3 were readily available, the development of amine 4 enabled pursuit of the strategy illustrated by the retrosynthetic tree, shown in FIG. 10. This divergent strategy, which involved attachment of a "module" (i.e., branched amine) to the appropriate acid terminated dendrimer gives facile access to nanoscale spheres with porous infrastructures.

Amine 4 was prepared from the branched trinitrile 5,[47] as shown in Scheme 1.

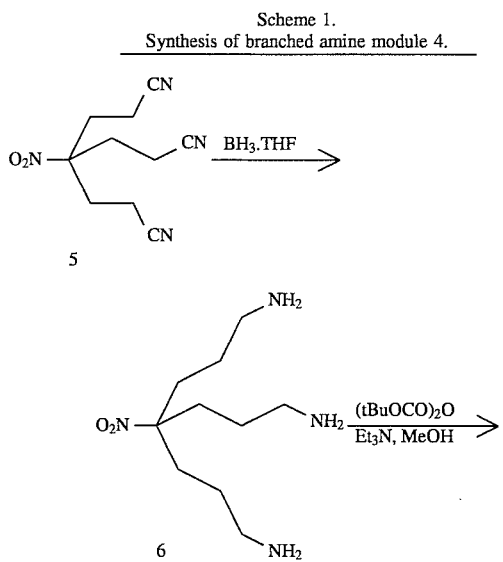

Scheme 1.
Synthesis of branched amine module 4.

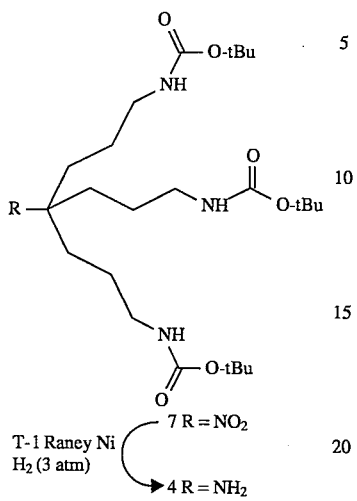

Borane reduction of 5 gave (82%) trimine 6 as indicated by a loss of the nitrile ($^{13}$C NMR) resonance at 119.3 ppm, the appearance of a peak at δ 42.5 (CH$_2$NH$_2$) and a ($^1$H NMR) triplet (CH$_2$NH$_2$, J=6.0 Hz, 6H) at 2.65 ppm. Treatment of triamine 6 with di-tert-butyl dicarbonate and Et$_3$N in refluxing MeOH gave (87%), after workup and purification via column (SiO$_2$)chromatography, tricarbamate 7. The $^{13}$C NMR spectrum of 7 possesses the expected seven peaks; signals at 28.3 (CH$_3$), 79.1 (CMe$^3$), and 156.0 (C=O) ppm correspond to the tert-butoxycarbonyl (Boc) moieties. Catalytic reduction (T-Raney Ni, H$_2$, 55 psi, 65° C., 12 hours) of 7 gave (92%) amine 4; reduction was confirmed by a shirt ($^{13}$C NMR) of the quaternary carbon resonance from 94.2 to 52.8 ppm.

The preparations of dodeca-tert-butylester 10, dodecaacid 11, 36-tert-butylester 16, 36-acid 17, 108-tert-butylester 22, and 108-acid 23 have been described;[48] complete synthetic details are given in the experimental synthesis section below. syntheses of the first generation dodeca- alcohol 9, acid 11, and amine 13 are depicted in Scheme 2.

Scheme 2.
Synthesis of the first generation cascade polyamides.

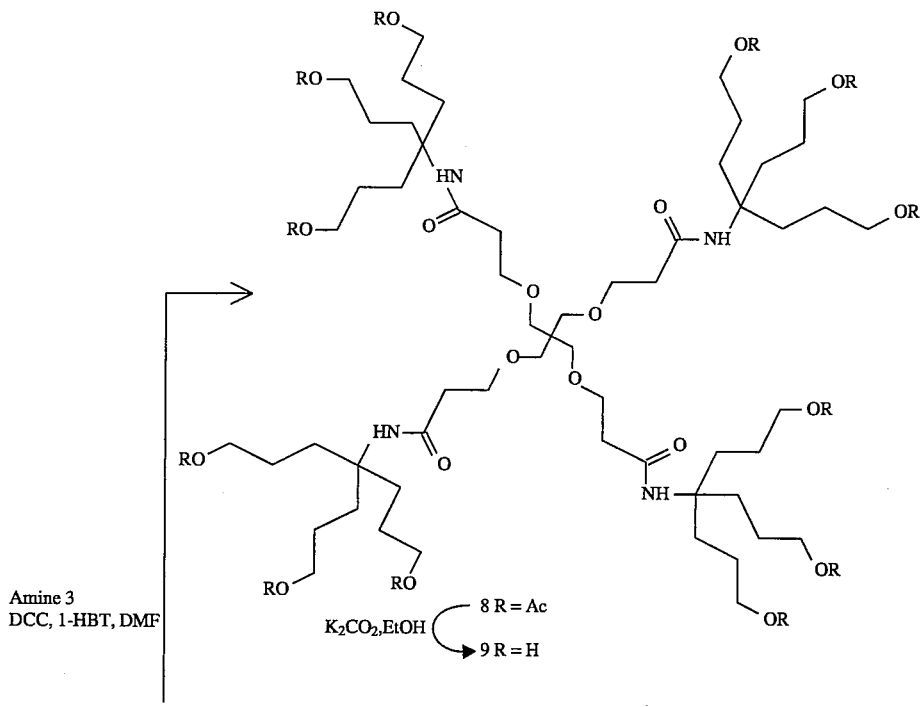

-continued
Scheme 2.
Synthesis of the first generation cascade polyamides.
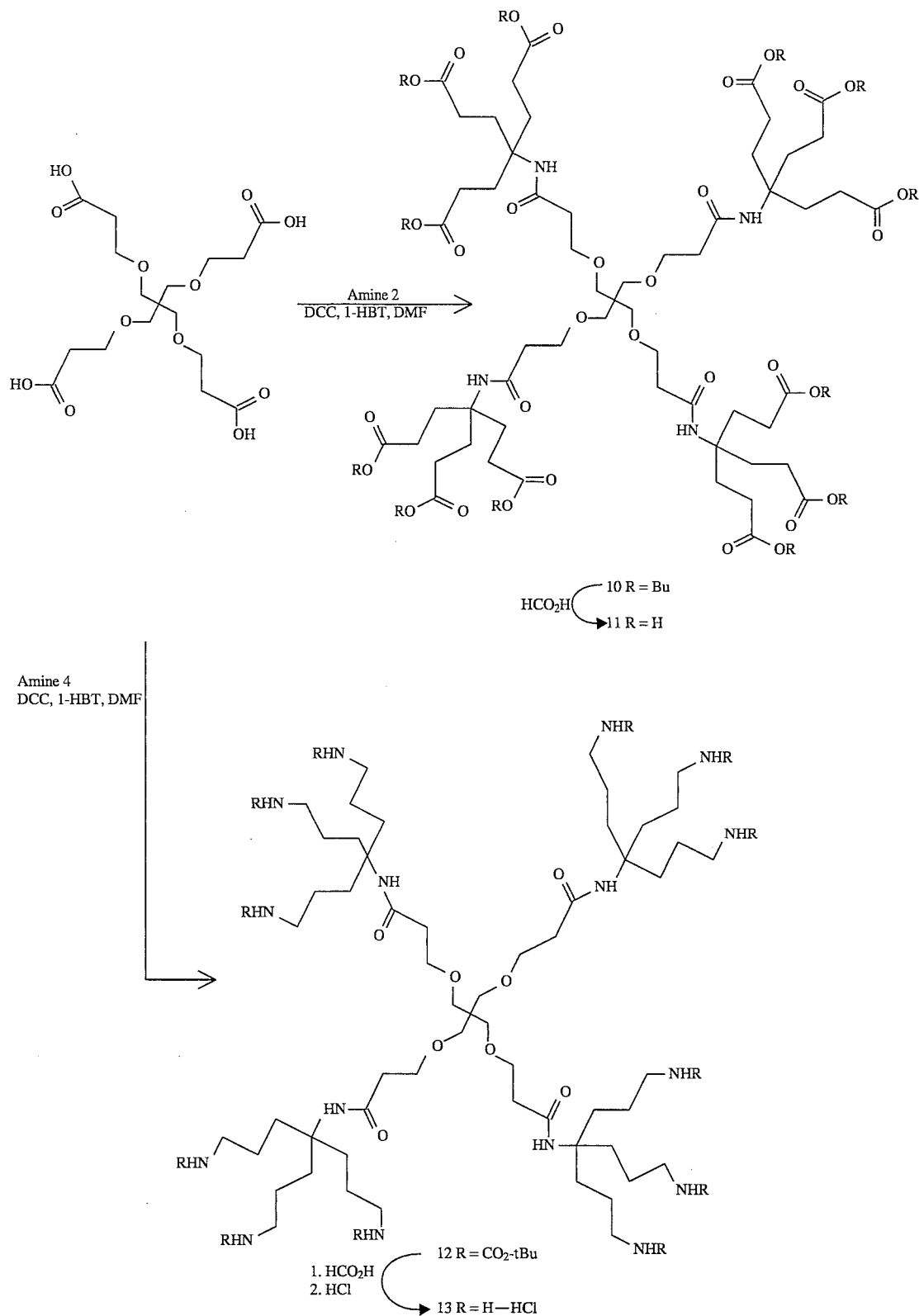

In each case, the tetraacid core 1 was aminated with the branched amine building block via standard dicyclohexyl-carbodiimdie[49,50/1]-hydroxybenzotriazole[51] (DCC/1-HBT) peptide coupling conditions, before facile removal of the protecting group. The second (Z=36) and third (Z=108) generation alcohol terminated cascades ("arborols") and amine terminated cascades were similarly prepared from dodecaacid 11 Scheme 3) and the second tier 36-acid (not shown), respectively.

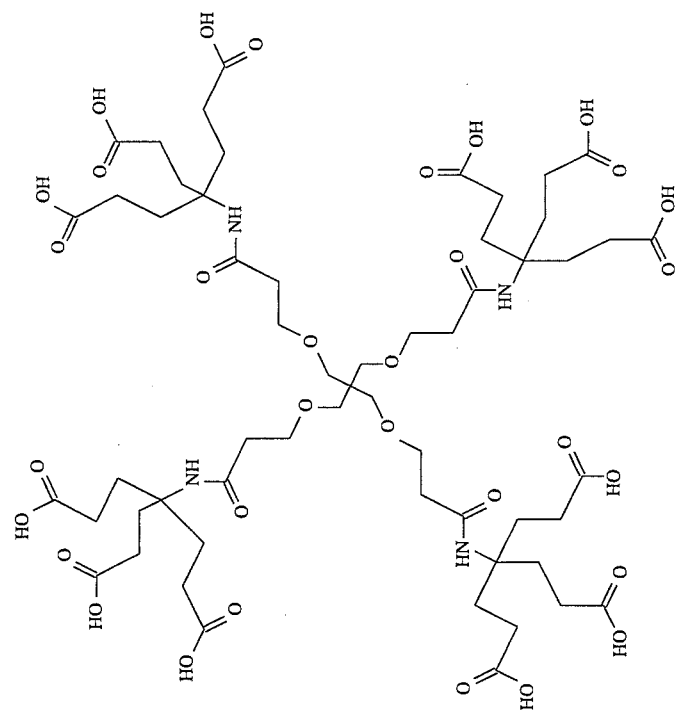
Scheme 3.
Synthesis of the second and third generation cascade polyamides.

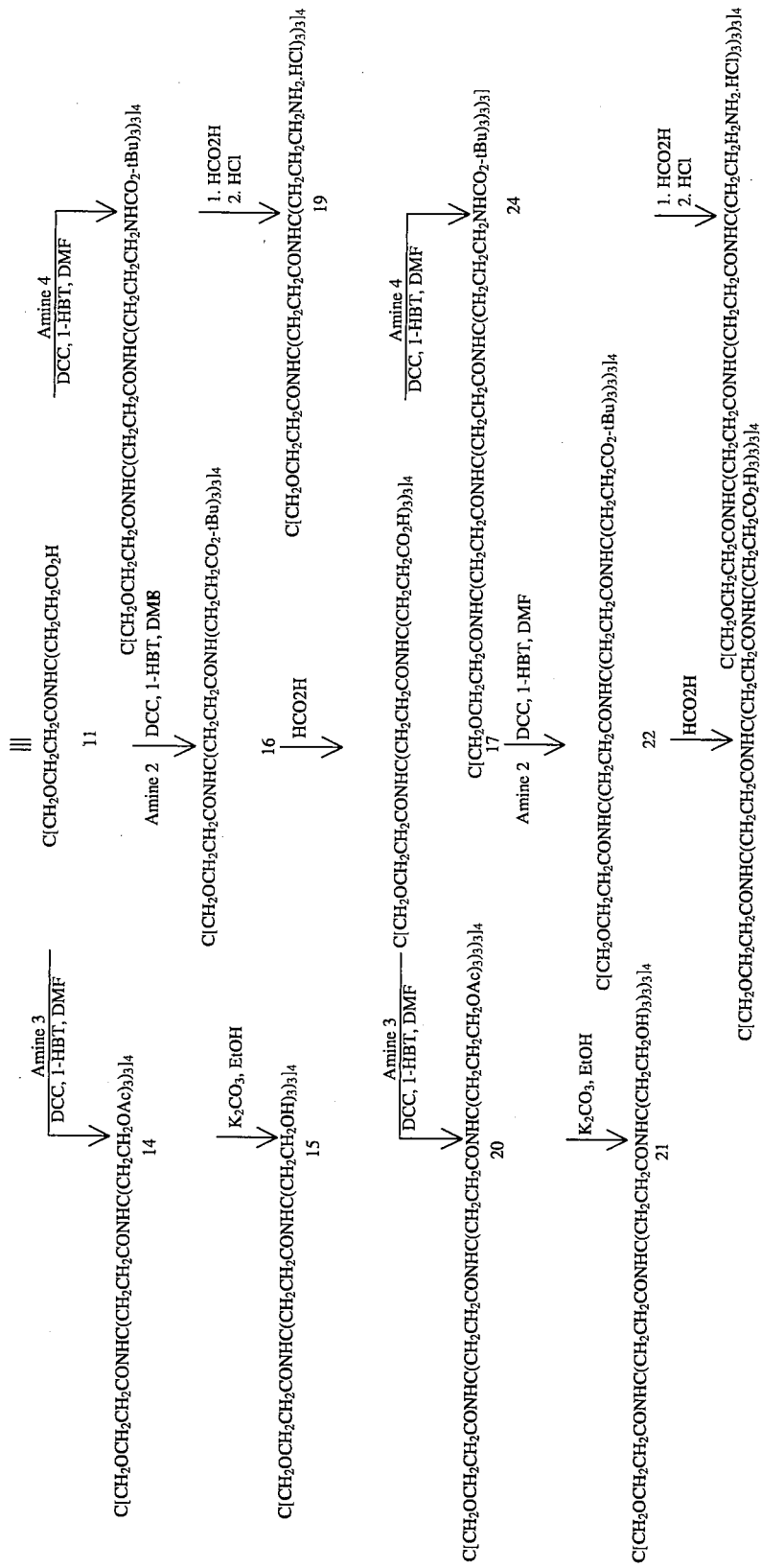

The first three generations of the alcohol terminated cascade polyamides were prepared having the general family name Z-Cascade:methane[4]:(3-oxo-6-oxa-2azaheptylidyne):(3-oxo-2-azapentylidyne)$^{G-1}$:propanol. Coupling of tetraacid 1 with amine 3 via treatment with DCC/1-HBT in DMF at 25° C. provided (47%) dodecaacetate 8, which was characterized by eleven ($^{13}$C NMR) resonances. Two ($^1$H NMR) triplets at 2.37 (CH$_2$CONH) and 3.63 (OCH$_2$) ppm and a singlet at 3.31 ($^{4°}$ C$_{Core}$CH$_2$O) ppm, which were attributed to the core of 8, gave proper integration relative to each other and to each of the resonances of the twelve exterior branches. Base-catalyzed transesterification of 8, followed by purification via dialysis, gave (36%) dodecaalcohol 9, as evidenced by the loss of the ($^1$H and $^{13}$C) NMR resonances and IR stretches attributed to the acetyl moieties. The relatively low yields for these materials are probably due to losses during dialysis. The formula weights of these materials are close to the molecular weight cut-off (MWCO) rating of the dialysis membrane. Coupling amine 4 to tetraacid 1 gave (56%) dodecaurethane 12, which was hydrolyzed in formic acid (95%) at 25° C. The formate salt was treated with dilute aqueous HCl and dialyzed to provide (37%) dodecaamine 13 as its hydrochloride salt. Again, the relatively low yields for these materials are probably due to losses during dialysis. The formula weights of these materials are close to the molecular weight cut-off (MWCO) rating of the dialysis membrane. The $^{13}$C NMR spectrum exhibited the expected nine resonances. The second generation 36-carbamate 18 and third generation 108-carbamate 24 were similarly prepared and deprotected to give 36-amine 19 and 108-amine 25, respectively. The $^1$H NMR spectra (D$_2$O) of 19 and 25 contained core methylene signals at 2.38, 3.21, and 3.54 ppm that gave proper integration relative to each other and to resonances at 1.73 and 2.16 ppm, attributed to the interior methylenes, and at 1.44, 1.58, and 2.82, corresponding to the methylene groups of the exterior branches.

H. Pulsed Field Gradient NMR Studies

The following experiments test the hydrodynamic effects of the environment on the expansion and contraction of the micelies. D$_2$O solutions containing an alcohol or amine terminated cascade polymer were examined by means of Diffusion Ordered 2D-NMR Spectroscopy (DOSY).[52] This method, which makes use of pulsed field gradient NMR (PFG-NMR), displays chemical shifts in one direction and diffusion coefficients in the other. As previously reported for the acid terminated polymer, the diffusion dimension revealed only the HOD peak and a single polymer peak. Therefore, data acquisition and analysis was focussed on the polymer peaks. In principal, the complete DOSY experiment requires no more time than a PFG-NMR experiment for one peak; however, the nuclear relaxation time $T_1$, is much longer for HOD than for the polymers and the repetition time required for acquisition of the complete DOSY data set is determined by the longest $T_1$ in the sample. Thus, to obtain the maximum signal to noise ratio, the experimental parameters were optimized for the polymer peaks at the expense of the uninteresting HOD signal.

Figure 11:
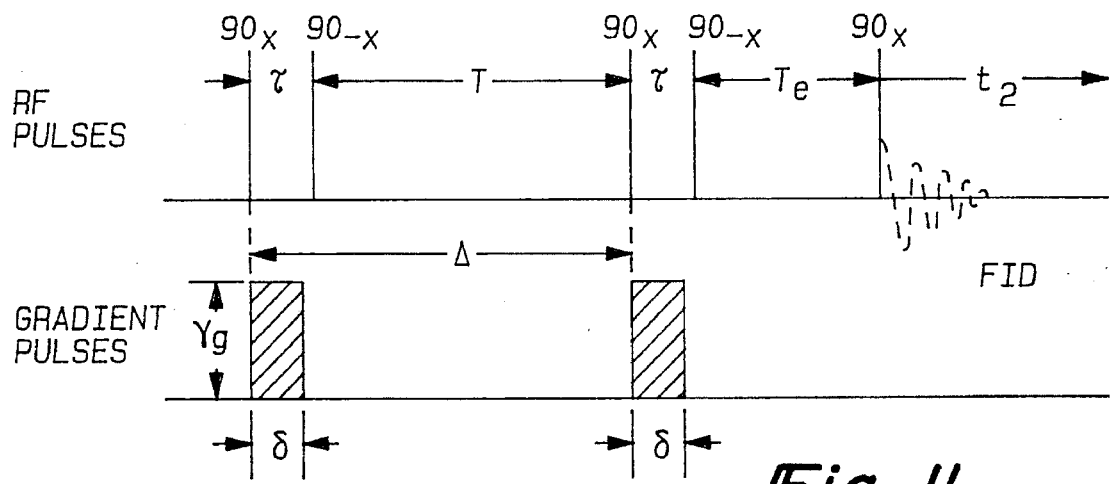
FIG. 11 is a basic LED pulse sequence, the gradient pulses being shown representing the last two pulses in a train of five matched and equally spaced pulses, phase cycling and sometimes homospoil pulses during $T_e$ being used to suppress secondary echoes.
Figure 12:
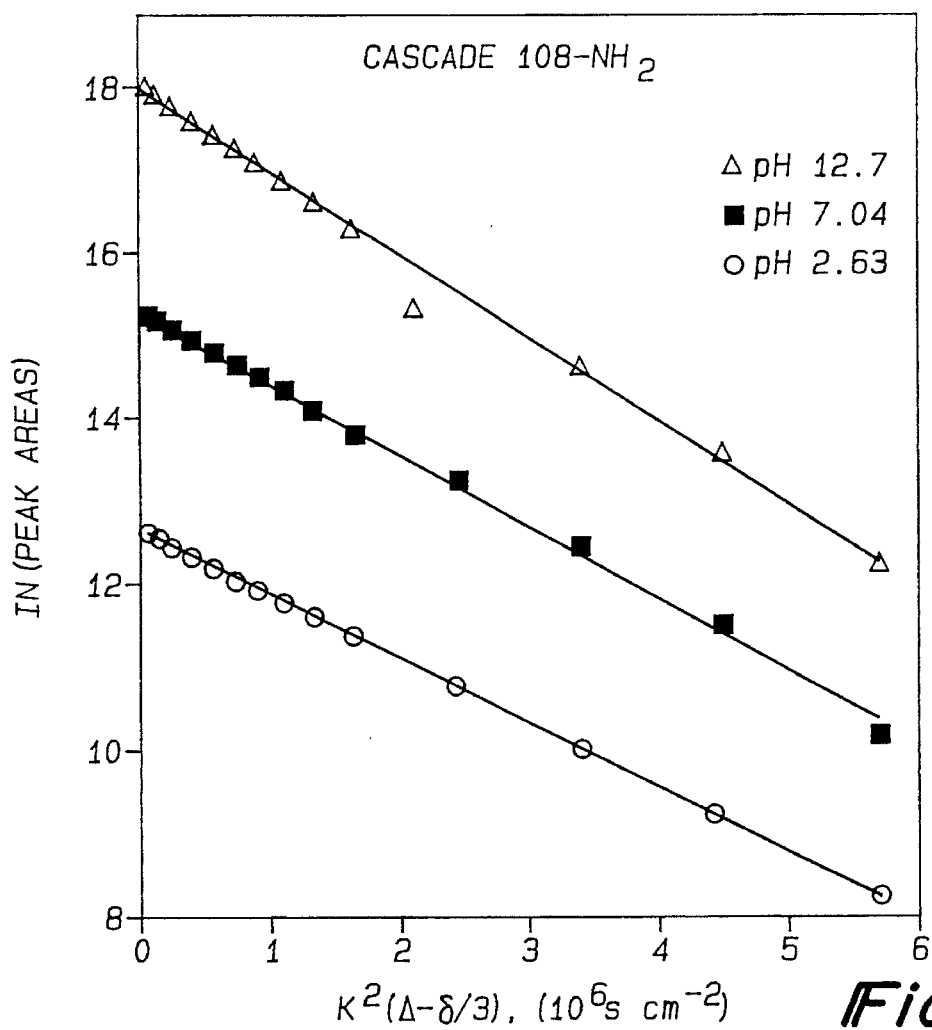
FIG. 12 is a graph wherein the are of the major polymer peaks versus $K^2$ ($\Delta$–$\delta$/3) for the cascade 108-amine polymer in acidic, neutral, and basic solutions at 298K.

All experiments were performed with the Longitudinal-Eddy-Current Delay pulse sequence (LED) shown in FIG. 11 to minimize distortions resulting from eddy currents and the effects of J-modulation[53]. An actively shielded gradient coil set was also used to minimize pulse induced eddy currents.[54] The DOSY data sets were acquired and analyzed as previously described.[52] Diffusion coefficients were obtained for each generation of the water soluble alcohol and amine terminated polyamines at ca. 1 mM concentration by using only the integral A of the major polymer peaks. A typical 1H 250 MHz data set is shown in FIG. 12 for the 108-amine cascade polymer. The integrals of the polymer peaks were fit by nonlinear regression to the Stejskal-Tanner equation.[55]

$$A=A_o \exp [-K^2\Delta-\delta 3)D] \quad (1)$$

with $A_o$ and the tracer diffusion coefficient D as free parameters. In Equation 1, $K=\gamma g\delta$, where $\gamma$ is the magnetogyric ratio, g and $\delta$ are the amplitude and duration of the gradient pulses, respectively, and $\Delta$ is the diffusion time (i.e., the time between the leading edges of the gradient pulses). In these experiments $\Delta$-100.0 ms and $\delta$=1.00 ms. Also, the rf pulse pair separation was $\tau$=1.60 ms and the eddy current delay period was $T_e$=20.0 or 25.0 ms. Effective hydrodynamic radii were calculated from measured D values with the Stokes-Einstein equation, $R_H$=kBT/(D6$\pi\eta$), where $k_B$ is the Boltzmann constant, T is the absolute temperature, and $\eta$=1,098 cp is the viscosity of D$_2$O at 298K.[56]

The measured diffusion coefficients and calculated hydrodynamic radii for the alcohol- and amine-terminated cascade polyamides are listed in Table 1.

TABLE 1

Observed diffusion coefficients and calculated hydrodynamic radii for the four-directional cascade polymers.

| Generation (G) | Number of Terminal Groups (Z) | Terminal Functionality | Formula Weight | [Cascade] (mM) | D(cm$^2$s$^{-1}$)/Hydrodynamic Radius (Å) | | |
|---|---|---|---|---|---|---|---|
| | | | | | Acidic pH | Neutral pH | Basic pH |
| 1 | 12 | —CO$_2$H$^a$ 10 | 1,341 | 1.00 | 2.41 × 10$^{-6}$ 8.24 | 1.62 × 10$^{-6}$ 12.3 | 1.68 × 10$^{-6}$ 11.8 |
| | | —CH$_2$OH$^b$ 9 | 1,174 | 1.00 | 2.30 × 10$^{-6}$ 8.64 | 2.33 × 10$^{-6}$ 8.53 | 2.35 × 10$^{-6}$ 8.46 |
| | | —CH$_2$NH$_2^c$ 13 | 1,162 | 1.00 | 1.68 × 10$^{-6}$ 11.8 | 1.75 × 10$^{-6}$ 11.4 | 1.92 × 10$^{-6}$ 10.3 |
| 2 | 36 | —CO$_2$H$^a$ 17 | 4,092 | 1.00 | 1.74 × 10$^{-6}$ 11.4 | 1.15 × 10$^{-6}$ 17.3 | 1.26 × 10$^{-6}$ 15.8 |
| | | —CH$_2$OH$^b$ 15 | 3,589 | 1.00 | 1.57 × 10$^{-6}$ 12.7 | 1.56 × 10$^{-6}$ 12.7 | 1.60 × 10$^{-6}$ 12.4 |
| | | —CH$_2$NH$_2^c$ 19 | 3,553 | 1.00 | 1.09 × 10$^{-6}$ 18.2 | 1.20 × 10$^{-6}$ 16.6 | 1.44 × 10$^{-6}$ 13.8 |
| 3 | 108 | —CO$_2$H$^a$ 23 | 12,345 | 1.00 | 1.15 × 10$^{-6}$ 17.3 | 8.32 × 10$^{-7}$ 23.9 | 9.09 × 10$^{-7}$ 21.9 |
| | | —CH$_2$OH$^b$ | 10,834 | 0.50 | 1.30 × 10$^{-6}$ | 1.28 × 10$^{-7}$ | 1.28 × 10$^{-7}$ |

TABLE 1-continued

Observed diffusion coefficients and calculated hydrodynamic radii for the four-directional cascade polymers.

| Genertion (G) | Number of Terminal Groups (Z) | Terminal Functionality | Formula Weight | [Cascade] (mM) | D(cm$^2$s$^{-1}$)/Hydrodynamic Radius (Å) Acidic pH | Neutral pH | Basic pH |
|---|---|---|---|---|---|---|---|
| | | 21 | | | 15.3 | 15.5 | 15.5 |
| | | —CH$_2$NH$_2$[c] | 10,728 | 1.00 | 7.90 × 10$^{-7}$ | 8.50 × 10$^{-7}$ | 1.07 × 10$^{-6}$ |
| | | 25 | | | 25.2 | 23.4 | 18.6 |
| 4 | 324 | —CO$_2$H[a] | 37,102 | 0.97 | 8.79 × 10$^{-7}$ | 6.01 × 10$^{-7}$ | 6.87 × 10$^{-7}$ |
| | | 27 | | | 22.6 | 33.1 | 28.9 |
| 5 | 972 | —CO$_2$H[a] | 111,373 | 0.34 | 7.83 × 10$^{-7}$ | 5.35 × 10$^{-7}$ | 6.17 × 10$^{-7}$ |
| | | 29 | | | 25.4 | 37.1 | 32.3 |

[a]Solution pH ranged 3.16–3.64, 7.01–7.04, and 13.24–13.33 for the acidic, neutral, and basic solutions, respectively.
[b]Solution pH ranged 2.28–4.74, 6.89–7.44 and 12.18–13.18 for the acidic, neutral, and basic solutions, respectively.
[c]Solution pH ranged 2.60–3.77, 7.04–7.10, and 12.10–12.69 for the acidic, neutral, basic solutions, respectively.

Unlike their acid-terminated parents, the alcohol-terminated cascades exhibited no appreciable pH dependence of their hydrodynamic radii. In contrast, the amine terminated polyamides exhibited a pH size dependence that is approximately equal, but opposite to, that displayed by the corresponding polyacids. The amines are "expanded" at acidic pH and "contracted" at basic pH, while the corresponding acids are largest ("expanded") at neutral pH and smallest ("contracted") at acidic pH (FIG. 10). Remarkably, the third generational 108-acid and 108-amine each undergo a maximum 35% change in hydrodynamic radius.

The branched amines 2,3, and 4 were used to prepare water-soluble cascade polymers, possessing identical internal hierarchical architectures, but with either acidic, neutral or basic terminal functional groups. The availability of these complementary series allowed an initial examination of the dependence of macromolecular properties on the nature of the cascade terminal group. The PFG NMR results are consistent with the supposition that size variations arise from columbic repulsions between charged terminal moieties, which are formed as a function of pH. These findings should be general in that dendritic macromolecules with other internal branching architectures and functional group linkages should also in a similar manner provided their interior branches are relatively flexible. As a consequence, the use of cascade polymers as size standards in aqueous solution must be tempered by this pronounced pH dependence.

I. Experimental Synthesis

General Comments. Melting point data were obtained in capillary tubes with a Gallenkamp melting point apparatus and are uncorrected. 1H and $^{13}$C NMR spectra were obtained in CDCl$_3$, except where noted, with Me$_4$Si as the internal standard (δ=0 ppm), and recorded at 360 MHz. Infrared spectra (IR) were obtained (KBr pellet, unless otherwise noted) and recorded in a Perkin-Elmer 621 grating infrared spectrometer. Mass spectral (MS) data were obtained by Burt Wolf (FSU) at 79 eV on a Finnigan 4510 GC-mass spectrometer and are reported as (assignment, relative intensity). Elemental analyses were performed by M-H-W Laboratories, Phoenix, Ariz.

Dialysis: Purification of the water soluble acid, alcohol, and amine terminated cascade polymers with molecular weights greater than 1000 was accomplished via dialysis (H$_2$O, 4 L, 12 h) using Spectra/Por® 6 molecularporous dialysis membranes (1000 MWCO). In a typical procedure for the cascade polyacids, five grams of crude polyacid were dissolved in water (50 mL) using 10% NaOH to assist in the dissolution. Additional base was added resulting in a yellow colored solution at approximately pH=7. The solution was poured in the appropriate length of dialysis membrane so that upon sealing the membrane tube was flaccid. The filled membrane was dialyzed against four liters of stirred deionized water for twelve hours, with replacement of the water at least once during that time. During dialysis, the solution changed from a deep to pale yellow color, an insoluble white suspension appeared in the solution, and the membrane tube became rigid. The contents of the tube were filtered and the water was removed in vacuo to provide the polysodiocarboxylate cascade as a white solid.

The alcohol cascades were dissolved in deionized water with no pH adjustment. The crude amine formate salts were dissolved in 2% HCl and each resulting solution was poured into a dialysis membrane, which was sealed and placed in water as quickly as possible to minimize degradation of the cellulose tubing that may occur under these acidic conditions.

Preparative HPLC: Small portions of the polyacids were subjected to preparative scale HPLC using an Isco Model 2350 HPLC Pump, Isco Model 2361 Gradient Programmer, Isco V$^4$® Absorbance Detector, Spectra-Physics SP-4600 Integrator, Cygnet® Fraction Collector, and a DuPont Zorbax® ODS (C$_{18}$-Octyldodecyl Sulfate, 21.2 mm×25 cm) column. The dialyzed polyacid was dissolved in water (ca. 75 mg/mL), titrated with 10% HCl to pH 3–4, and filtered through a 0.02 micron Anotop® alumina matrix filter before injection (2 mL). The gradient conditions were 2 min. water followed by a 15 min. linear ramp to 60/40 H$_2$O/CH$_3$CN. The retention time for the product was approximately 10 min at a flow rate of 20 mL/min, which corresponded to an operating pressure of 1,400 psi.

1,7-Diamino-4-(3-aminopropyl)-4-nitroheptane (6) was prepared as previously reported.[51]

1,7-Di-[N-tert-butoxycarbonyl)amino]-4-[3-(N-tert-butoxycarbonyl)-aminopropyl]-4-nitroheptane (7). A mixture of triamine 6 (4.06 g, 17.5 mmol), Et$_3$N (5.56 g, 54.9 mmol), and di-tert-butyl dicarbonate (12.00 g, 55.0 mmol) in MeOH (60 mL) was refluxed for 2 hours before the solvent was removed in vacuo. The resulting residue was column chromatographed (SiO$_2$) eluting with 10% MeOH in EtOAc to provide (87%) tricarbamate 7, as a slightly hygroscopic white solid: 8.05 g; mp 48°–51° C.; $^1$H NMR δ1.44(s, CH$_3$ and CH$_2$CH$_2$CH$_2$, 33H), 1.90 (t, J=7.2 Hz $^{4°}$CCH$_2$, 6H), 3.10 (t, J=5.0 Hz CH$_2$NH, 6H), 4.72 (br, NH, 3H); $^{13}$C NMR δ24.2 (CH$_2$CH$_2$CH$_2$), 28.3 (CH$_3$), 32.6 ($^{4°}$CCH$_2$), 40.1 (CH$_2$NH), 79.1 (CMe$_3$), 94.2 ($^{4°}$CHO$_2$), 156.0 (CO); IR 3358 (NH), 1687 (C=O) 1543 (NO$_2$), 1172 (C—O) cm$^{-1}$.
Anal. Calcd for C$_{25}$H$_{48}$N$_4$O$_8$: C, 56.37; H, 9.08; N, 10.52.

Found: C, 56.76; H, 8.84; N, 10.50. MS m/e 533.2 (M$^+$+1, 26).

1,7-Di-[N-tert-butoxycarbonyl)amino]-4-[3-(N-tert-butoxycarbonyl)aminopropyl]-4-aminoheptane (4). A slurry of nitro tricarbamate 7 (8.06 g, 15.1 mmol), T-1 Raney Ni (10 g), and absolute EtOH (300 mL) was hydrogenated at 55 psi and 60° C. for 12 hours. The solution was cautiously filtered through Celite, to remove the catalyst, and the solvent removed in vacuo to give (92%) the amino tricarbamate 4, as a hygroscopic white solid: 7.60 g; $^1$H NMR δ1.33 (m, $CH_2CH_2CH_2$, 6H), 1.44 (s, $CH_3$ and $^{4°}CCH_2$, 33H), 3.10 (br, $CH_2NH$, 6H), 4.77 (br CONH, 3H); $^{13}C$ NMR δ24.1 ($CH_2CH_2CH_2$), 28.3 ($CH_3$), 36.9 ($^{4°}CCH_2$), 40.9 ($CH_2NH$), 52.8 ($^{4°}CNH_2$), 79.0 ($CMe_3$), 155.9 (CO); IR (neat) 3355 ($NH_2$, NH), 1694 (C=O), 1170 (C—O) cm$^{-1}$. Anal. Calcd for $C_{25}H_{50}N_4O_6$: C, 59.73; H, 10.02; N, 11.14. Found: C, 59,63; H, 9.85; N, 10.95. MS m/e 503.03 (M$^+$+1, 25).

12-Cascade:methane[4]:(3-oxo-6-oxa-2-azaheptylidyne-):tert-butyl propanoate (10). General Procedure A. A mixture of tetraacid 1 (9.73 g, 23 mmol), amine 2 (40.00 g, 96 mmol), dicyclohexylcarbodiimide (DCC: 19.80 g, 96 mmol), and 1-hydroxybenzotriazole (1-HBT: 13.00 g, 96 mmol) in DMF (350 mL) was stirred at 25° C. for 24 hours. After filtration to remove dicyclohexylurea, the solvent was evaporated in vacuo to give a residue, which was dissolved in EtOAc (200 mL), then sequentially washed with cold aqueous HCl (10%), water, aqueous NaHCO$_3$ (10%), and brine. The organic phase was dried (MgSO$_4$), concentrated in vacuo, and chromatographed (SiO$_2$ column) eluting with 10% EtOAc in CH$_2$Cl$_2$ to furnish (70%) the desired 12-cascade ester 10, as a spongy white solid: 32.33 g; mp 68°–72° C.; $^1$H NMR δ1.43 (s, $CH_3$, 108H), 1.96)t, J=7.2 Hz, $CH_2CH_2COO$, 24H), 2.22 (t, J=7.2 Hz, $CH_2COO$, 24H), 2.38 (t, J=5.7 Hz, $CH_2CONH$, 8H), 3.34 (s, $CH_2O$, 8H), 3.67 (t, J=5.7 Hz, $OCH_2$, 8H), 6.38 (s, NH, 4H); $^{13}C$ NMR δ28.1 ($CH_3$), 29.7 ($CH_2CH_2COO$), 37.4 ($CH_2COHN$), 45.4 ($^{4°}C_{Core}$), 57.3 ($^{4°}CNH$), 67.7 ($CH_2O$), 68.9 ($OCH_2$), 80.4 ($CMe_3$), 170.7 (CONH), 172.7 ($CO_2$); IR 3310 (NH), 1733 (ester C=O), 1664 (amide C=O), 1157 (ester C—O)cm$^-$. Anal. Calcd for $C_{105}H_{184}N_4O_{32}$; C, 62.60; N, 9.20; N, 2.78. Found: C, 62.82; H, 9.14; N, 2.91.

12-Cascade:methane[4]:(3-oxo-6-oxa-2-azaheptylidyne);propanoic acid (11). General Procedure B. A solution of dodecaester 10 (30.00 g, 15 mmol) in 95% formic acid (100 mL) was stirred at 25° C. for 12 hours. After concentration, toluene (50 mL) was added and the solution was again evaporated in vacuo to azeotropically remove residual formic acid. The crude solid was dissolved in a water (200 mL)/acetone (10 mL) mixture and then sequentially washed with CH$_2$Cl$_2$ (50 mL) and EtOAc (50 mL). The aqueous phase was boiled with activated charcoal (0.5 g), filtered through Celite, and then concentrated in vacuo to furnish the acid as a white solid, which was purified via dialysis and preparative reverse-phase HPLC to give (72%) dodecaacid 11, as a white solid: 14.38 g; mp 64°–66° C.; $^1$H NMR (D$_2$O/p-dioxane/3.54 ppm) δ1.76 (t, J=7.5 Hz, $CH_2CH_2COO$, 24H), 2.04 (t, J=7.5 Hz, $CH_2COO$, 24H), 2.24 (br, $CH_2CONH$, 8H), 3.15 (br, $CH_2O$, 8H), 3.44 (br, $OCH_2$, 8H; $^{13}C$ NMR (D$_2$O/p-dioxane/66.4 ppm) δ29.7 ($CH_2CH_2COO$), 30.1 ($CH_2COO$), 37.0 ($CH_2CONH$), 45.0 ($^{4°}C_{Core}$), 57.8 ($^{4°}CNH$), 67.6 ($CH_2O$), 69.8 ($OCH_2$), 173.0 (CONH), 179.2 ($CO_2H$); IR 3366 (br, acid OH), 1720 (acid C=O), 1645 (amide C=O) cm$^{-1}$. Anal. Calcd for $C_{57}H_{88}N_4O_{32}$; C, 51.04; H, 6.61; N, 4.18. Found: C, 50.89; H, 6.83; N, 4.38.

36-Cascade:methane[4]:(3-oxo-6-oxa-2-azaheptylidyne):(3-oxo-2-azapentylidyne):tert-butyl propanoate (16) was prepared (57%), as a spongy white solid, from dodecaacid 11 (5.63 g, 4.2 mmol), amine 2 (21.98 g, 52.9 mmol), DCC (10.89 g, 52.9 mmol) 1-HBT (7.14 g, 52.9 mmol), and DMF (250 mL) via Procedure A: 14.55 g; mp 67°–70° C.; $^1$H NMR δ1.42 (s, $CH_3$, 324H), 1.95, 2.20 (m, $CH_2CH_2CO$, 192H), 2.37 (t, J=5.7 Hz, $OCH_2CH_2CO$, 8H), 3.32 (s, $CH_2O$, 8H), 3.66 (t, J=5.7 Hz, $OCH_2$, 8H), 6.36 (s, NH, 16H); $^{13}C$ NMR δ28.1 ($CH_3$), 29.7 ($CH_2CH_2CO$), 37.4 ($OCH_2CH_2CO$), 45.4 ($^{4°}C_{Core}$), 57.3 ($^{4°}CNH$), 67.7 ($CH_2O$), 68.9 ($OCH_2$), 80.4 ($CMe_3$), 170.7 (CONH), 172.6 ($CO_2$); IR 3311 (NH), 1730 (ester C=O), 1661 (amide C=O), 1157, (ester C—O) cm$^{-1}$. Anal. Calcd for $C_{321}H_{556}N_{16}O_{92}$: C, 63.08; H, 9.17; N, 3.67. Found: C, 63.18; H, 8.89; N. 3.79.

36-Cascade:methane[4]:(3-oxo-6-oxa-2-azaheptylidyne):(3-oxo-2-asapentylidyne):propanoic acid(17) was prepared (77%) by hydrolysis of 36-ester 16 (13.55 g, 2.22 mmol) via Procedure B: 6.95 g; mp 132°–134° C.; $^1$H NMR (5% NaOD/p-dioxane/3.54 ppm) δ1.75, 1.99 (br, $CH_2CH_2CO$, 192H), 2.32 (br, $OCH_2CH_2CO$, 8H), 3.19 (br, $CH_2O$, 8H), 3.48 (br, $OCH_2$, 8H); $^{13}C$ NMR (5% NaOD/p-dioxane/66.4 ppm) δ29.7, 30.1 ($CH_2CH_2CO$), 37.0 ($OCH_2CH_2CO$), 45.0 (°$C_{Core}$, 57.9, 58.1 ($^{4°}CNH$), 67.7 ($CH_2O$), 69.9 ($OCH_2$), 173.1 (CONH), 179.7 ($CO_2$); IR 3363 (br, acid OH), 1718 (acid C=O), 1648 (amide C=O) cm$^{-1}$. Anal. Calcd for $C_{177}H_{268}N_{16}O_{92}$: C, 51.95; H, 6.60; N, 5.48. Found: C, 51.74; H, 6.71; N, 5.30.

108-Cascade:methane[4]:(3-oxo-6-oxa-2-azaheptylidyne):(3-oxo-2-azapentylidyne)$^2$:tert-butyl propaneate (22) was prepared (48%), as a spongy white solid from 36-acid 17 (2.63 g, 643 μmol), amine 2 (10.10 g, 24.3 mmol), DCC (5.00 g, 24.3 mmol), 1-HBT (3.28 g, 24.3 mmol), and DMF (150 mL) via Procedure A: 5.68 g; mp 103°–108° C. $^1$H NMR δ1.43 (s, $CH_3$, 972H), 1.95, 2.19 (br, $CH_2$, 624H); $^3$C NMR δ28.1 ($CH_3$), 29,7 ($CH_2CH_2$), 57.3 ($^{4°}CNH$), 80.3 ($CMe_3$), 170.8 (CONH), 172.7 ($CO_2$); IR 3366 (NH), 1730 (ester C=O), 1645 (amide C=O), 1160 (ester C—O) cm$^{-1}$. Anal. Calcd for $C_{969}H_{1,672}N_{52}O_{272}$: C, 63.24; H, 9.16; N. 3.96. Found: C, 63.06; H, 8.89; N, 4.23.

108-Cascade:methane[4]:(3-oxo-6-oxa-2-azaheptylidyne):(3-oxo-2-azapentylidyne)$^2$:propanoic acid (23) was prepared (70%) by hydrolysis of 108-ester 22 (5.68 g, 309 μmol) via Procedure B: 2.65 g; mp 136°–139° C.; $^1$H NMR (5% NaOD/p-dioxane/3.54 ppm) δ1.71, 1.92 (br, $CH_2CH_2CO$, 624H), 2.34 (br, $OCH_2CH_2CO$, 8H), 3.22 (br, $CH_2O$, 8H), 3.48 (br, $OCH_2$, 8H); $^{13}C$ NMR (5% NaOD/p-dioxane/66.4 ppm) δ31.0, 31.4 (br, $CH_2CH_2CO$), 58.3 (br, $^{4°}CNH$) 174.8 (CONH), 181.8 ($CO_2$); IR 3361 (br, acid OH), 1718 (acid C=O), 1647 (amide C=O) cm$^{-1}$. Anal. Calcd for $C_{537}H_{808}N_{52}O_{272}$: C, 52.25; H, 6.60; N, 5.90. Found: C, 52.06; H, 6.71; N; 5.76.

324-Cascade:methane[4]:(3-oxo-6-oxa-2-azapheptylidyne):(3-oxo-2-azapentylidyne)$^3$-tert-butyl propanoate (26) was prepared (42%), as a spongy white solid, from 108-acid 23 (5.39 g, 437 μmol), amine 2 (20.00 g, 48.1 mmol), DCC (9.91 g, 48.1 mmol), 1-HBT (6.50 g, 48.1 mmol), and DMF (250 mL) via Procedure A: 10.20 g; mp 135°–141° C.; $^1$H NMR δ1.39 (s, $CH_3$, 2916H), 1.93–2.17 (m, $CH_2$, 1920H); $^{13}C$ NMR δ28.1 ($CH_3$), 29.6 ($CH_2CH_2$), 57.2 ($^{4°}CNH$), 80.1 ($CMe_3$), 170.8 (CONH), 172.6 ($CO_2$; IR 3368 (NH), 1728 (ester C=O), 1658 (amide C=O), 1160 (ester C—O) cm$^{-1}$. Anal. Calcd for $C_{2913}H_{5020}N_{160}O_{812}$: C, 63.29; H, 9.15; N, 4.05. Found: C, 63.47; H, 8.99; N, 4.16.

324-Cascade:methane[4]:(3-oxo-6-oxa-2-azaheptylidyne):(3-oxo-2-azapentylidyne)$^3$:propanoic acid (27) was prepared (72%), as a white solid by hydrolysis of 324-ester 26 (5.00 g, 90.4 μmol) via Procedure B: 2.42 g; mp 138°–142° C.; $^1$H NMR (5% NaOD/p-dioxane/3.54 ppm)

δ1.71–1.93 (br, CH$_2$CH$_2$CO, 1920H), 2.38 (br, OCH$_2$CH$_2$, 8H), 3.22 (br, CH$_2$O, 8H), 3.48 (br, OCH$_2$, 8H); $^{13}$C NMR (5% NaOd/p-dioxane/66.4 ppm) δ29.7, 30.8 (br, CH$_2$CH$_2$CO), 57.4 ($^{4°}$CNH), 174.3 (CONH), 182.0 (CO$_2$H); IR 3361 (br, acid OH), 1720 (acid C—O), 1648 (amide C=O) cm$^{-1}$. Anal. Calcd for C$_{1617}$H$_{2428}$N16O0$_{812}$: C, 52.35; H, 6.60; N, 6.04. Found: C, 52.42; H, 6.60; N, 6.05.

972-Cascade:methane[4]:(3-oxo-6-oxa-2-azaheptylidyne):(3-oxo-a-azapentylidyne)$^4$:tert-butyl propanoate (28) was prepared (45%), as a spongy white solid, from 324-acid 27 (5.40 g, 146 μmol), amine 2 (20.00 g, 48.1 mmol), DCC (9.91 g, 48.1 mmol), 1-HBT (6.50 g, 48.1 mmol), and DMF (250 mL) via Procedure A: 10.87 g; mp 138°–142° C.; $^1$H NMR δ1.39 (s, CH$_3$, 8748H), 1.93–2.17 (m, CH$_2$, 5808H); $^{13}$C NMR δ28.0 (CH$_3$), 29.5 (CH$_2$CH$_2$), 57.4 ($^{4°}$CNH), 80.4 (CMe$_3$), 170.4 (CO$_2$), 172.6 (CONH); IR 3310 (NH), 1730 (ester C=O), 1645 (amide C=O), 1155 ester C—O) cm$^{-1}$. Anal. Calcd for C$_{8745}$H$_{15064}$N484O$_{2432}$:C, 63.31; H, 9.15; N, 4.09. Found: C, 63.47; H, 9.31; N, 4.04.

972-Cascade:methane[4]:(3-oxo-6-oxa-2-azaheptylidyne):(3-oxo-2-azapentylidyne)$^4$:propanoic acid was prepared (68%), as a white solid, by hydrolysis of 972-ester 28 (9.50 g, 57.3 μmol) via Procedure B: 4.34 g; mp 144°–149° C.; $^1$H NMR (5% NaOD/p-dioxane/3.54 ppm) δ1.38–3.50 (br, CH$_2$CH$_2$); $^{13}$C NMR (5% DaOD/p-dioxane/66.4 ppm) δ28.4, 29.5 (CH$_2$CH$_2$CO$_2$H), 56.5 ($^{4°}$CNH), 172.3 (CONH), 174.8 (CO$_2$); IR 3419 (br, acid OH), 1718 (acid C=O), 1638 (amide C=O) cm$^{-1}$. Anal. Calcd for C$_{4857}$H$_{7288}$N484O$_{2432}$: C, 52.38; H. 6.60; N, 6.09. Found C, 52.24; H, 6.70; N, 6.03.

12-Cascade:methane[4]:(3-oxo-6-oxa-2-azaheptylidyne):1-acetoxypropane (8). General Procedure C. A mixture of tetraacid 1 (433 mg, 1.02 mmol), 1-HBT (562 mg. 4.16 mmol), and DCC (858 mg, 4.16 mmol) in DMF (20 mL) was stirred at 0° C. for 1 hour. Amine 3 (1.38 g, 4.16 mmol) in DMF (10 mL) was added to the mixture, which was then stirred at 25° C. for an additional 23 hours. After filtration of dicyclohexylurea, the solvent was removed in vacuo to give an oily residue, which was column chromatographed (SiO$_2$) eluting with MeOH/EtOAc (5:95) to give 47%) dodecaester 8 as a fruity-smelling, hygroscopic, waxy, white solid: 811 mg; $^1$H NMR δ1.57 (m, CH$_2$CH$_2$CO, 24H), 1.74 (t, J=7.3 Hz, $^{4°}$CNHCH$_2$, 24H), 2.05 (s, CH$_3$, 36H), 2.37 (t, J=5.8 Hz, CH$_2$CONH, 8H), 3.31 (s, $^{4°}$C$_{Core}$CH$_2$O, 8H), 3.63 (t, J=5.8 Hz, OCH$_2$CH$_2$, 8H), 4.04 (t, J=6.3 Hz CH$_2$OAc, 24H), 5.92 (s, NH, 4H); $^{13}$C NMR δ20.9 (CH$_2$CH$_2$CH$_2$), 22.6 ($^{4°}$CNHCH$_2$), 31.0 (CH$_3$), 37.5 (CH$_2$CONH), 45.4 ($^{4°}$C$_{Core}$), 57.8 ($^{4°}$CNH), 64.4 (CH$_2$OAc), 67.7 ($^{4°}$C$_{Core}$CH$_2$), 67.7 ($^{4°}$C$_{Core}$CH$_2$), 69,2 OCH$_2$CH$_2$CONH, 170.3 (CONH), 171.0 (COO); IR (neat) 3397 (NH), 738 (ester C=O), 1643 (amide C=O), 1245 (ester C=O) cm$^{-1}$. Anal. Calcd for C$_{81}$H$_{136}$N$_4$O$_{32}$: C, 57.98; H, 8.17; N, 3.34. Found: C, 58.06; H, 8.35; N, 3.37.

12-Cascade:methane[4]:(3-oxo-6-oxa-2-azaheptylidnye:propanol (9). General Procedure D. A stirred slurry of dodecaester 8 (600 mg, 358 mmol), and K$_2$CO$_3$ (100 mg, 723 mmol) in absolute EtOH was refluxed. After 12 hours, the solution was filtered and the solvent removed in vacuo to give a residue, which was dissolved in water (20 mL) and dialyzed (H$_2$O, 4 L, 12 h) using a 1,000 MWCO Spectra/ Pro® 6 molecularporous membrane. Removal of the water in vacuo gave (36%) dodecaalcohol 9 as a clear, colorless, waxy solid: 149 mg; $^1$H NMR (D$_2$O/p-dioxane/3.54 ppm) δ1.29 (br, CH$_2$CH$_2$CH$_2$, 24H), 1.51 (br, $^{4°}$CNHCH$_2$, 2.26 (br, CH$_2$CONH, 8H), 3.20 (s, $^{4°}$C$_{Core}$CH$_2$, 8H), 3.44 (br, CH$_2$OAc, 24H), 3.48 (br, OCH$_2$CH$_2$CONH, 8H); $^{13}$C NMR (D$_2$O/p-dioxane/66.4 ppm) δ25.4 (CH$_2$CH$_2$CH$_2$), 30.6 ($^{4°}$C.NHCH$_2$), 36.9 (CH$_2$CONH), 45.1 ($^{4°}$CNH), 61.9 (CH$_2$OAc), 67.7 ($^{4°}$C$_{Core}$CH$_2$), 69.4 (OCH$_2$CH$_2$CONH), 172.8 CONH); IR (neat) 3343 (OH), 1648 (amide C=O), 1059 (C—O) cm$^{-1}$. Anal. Calcd for C$_{57}$H$_{112}$N$_4$O$_{20}$; C, 58.34; H, 9.62; N, 4.77. Found: C, 58.39; H, 9.54; N, 4.59.

36-Cascade:methane[4]:(3-oxo-6-oxa-2-azaheptylidyne):(3-oxo-2-azapentylidyne):3-acetoxypropane (14) was prepared (50%), as a fruity-smelling, hygroscopic, waxy, white solid, from dodecaacid 11 (456 mg, 340 μmol), amine 3 (1.38 g, 4.16 mmol), DCC (858 mg, 4.16 mmol), 1-HBT (562 mg, 4.16 mmol), and DMF (30 mL) via Procedure C: 867 mg; $^1$H NMR δ1.52 (br, CH$_2$CH$_2$CH$_2$, 72H), 1.68 (br, CH$_2$CH$_2$CH$_2$, 72H) 1.91, 2.19 (br, $^{4°}$CNHCH$_2$CH$_2$CONH, 48H), 2.02 (s, CH$_3$, 108H), 2.34 (br, OCH$_2$CH$_2$CONH, 8H), 3.28 (s, $^{4°}$C$_{Core}$CH$_2$O, 8H), 3.58 (br, OCH$_2$CH$_2$, 8H), 4.00 (t, J=6.2 Hz, CH$_2$OAc, 72H); $^{13}$C NMR δ20.9 (CH$_2$CH$_2$CH$_2$), 22.5 ($^{4°}$CNHCH$_2$), 30.9 (CH$_3$), 31.4 ($^{4°}$CNHCH$_2$CH$_2$CONH), 37.4 (OCH$_2$CH$_2$CONH), 45.1 ($^{4°}$C$_{Core}$), 57.7, 57.8 ($^{4°}$CNH), 64.4 (CH$_2$OAc), 67.8 ($^{4°}$C$_{Core}$CH$_2$), 69.4 (OCH$_2$CH$_2$CONH), 171.4 (COO), 172.6 (CONH); IR (neat) 3376 (NH), 1738 (ester C=O), 1658 (amide C=O), 1247 (ester C—O) cm$^{-1}$. Anal. Calcd for C$_{249}$H$_{419}$N$_{16}$O$_{92}$; C, 58.62; H, 8.14; N, 4.39. Found. C, 58.53; H, 8.33; N, 4.49.

36-Cascade:methane[4]:(3-oxo-6-oxa-2-azaheptylidyne):(3-oxo-2-azapentylidyne):propanol (15) was prepared (72%), as a hygroscopic white solid, from 36-ester 14 (700 mg, 137 μmol) via Procedure D: 492 mg; mp 58°–60° C.; $^1$H NMR (D$_2$O/p-dioxane/3.54 ppm) δ1.25 (br, CH$_2$CH$_2$CH$_2$, 72H), 1.48 (br, CH$_2$CH$_2$CH$_2$, 72H), 1.72 (br, $^{4°}$CNHCH$_2$CH$_2$CONH, 24H), 1.95 (br, 4°CNHCH$_2$CH$_2$CONH, 24H), 2.27 (br, OCH$_2$CH$_2$CONH, 8H), 3.16 (br, $^{4°}$C$_{Core}$CH$_2$, 8H), 3.36 (br, CH$_2$OH, 72H), 3.46 (br, OCH$_2$CH$_2$CONH, 8H); $^{13}$C NMR (D$_2$O/p-dioxane/ 66.4 ppm) δ25.3 (CH$_2$CH$_2$CH$_2$), 30.4 (CH$_2$CH$_2$CH$_2$), 30.8 ($^{4°}$CNHCH$_2$CH$_2$CONH), 36.7 (OCH$_2$CH$_2$CONH), 45.0 ($^{4°}$C$_{Core}$), 57.8, 58.4 ($^{4°}$CNH), 61.8 (CH$_2$OH), 67.8 ($^{4°}$C$_{Core}$CH$_2$), 69.2 (OCH$_2$CH$_2$CONH), 174.5 (CONH); IR 3394 (OH), 1651 (amide C=O), 1059 (C—O) cm$^{-1}$. Anal Calcd for C$_{177}$H$_{340}$N$_{16}$O$_{56}$: C, 59.24; H, 9.55; N, 6.24. Found. C, 59.54; H, 9.38; N, 5.99.

108-Cascade:methane[4]:)3-oxo-6-oxa-2-azaheptylidyne):3-oxo-2-azapentylidyne)$^2$:1-acetoxypropane (20) was prepared (69%), as a fruity-smelling, hygroscopic, waxy, white solid, from 36-acid 17 (405 mg, 99.0 μmol), amine 3 (1.24 g, 3.74 mmol), DCC (771 mg, 3.74 mmol), 1-HBT (505 mg, 3.74 mmol), and DMF (30 mL) via Procedure C: 1.05 g; $^1$H NMR δ1.56 (br, CH$_2$CH$_2$CH$_2$, 216H), 1.72 (br, CH$_2$CH$_2$CH$_2$, 216H), 2.05 (s, CH$_3$, 324H), 4.03 (br, CH$_2$OAc, 216H); $^{13}$C NMR δ20.9 (CH$_2$CH$_2$CH$_2$), 22.5 ($^{4°}$CNHCH$_2$), 30.8 (CH$_3$), 31.4 ($^{4°}$CNHCH$_2$CH$_2$CONH), 37.4 (OCH$_2$CH$_2$CONH), 57.8 ($^{4°}$CNH), 64.5 (CH$_2$OAc), 67.8 ($^{4°}$C$_{Core}$CH$_2$), 69.4 (OCH$_2$CH$_2$CONH), 171.1 (COO), 172.5 (CONH); IR (neat) 3376 (OH), 1738 (ester C=O), 1661 (amide C=O), 1244 (ester C—O) cm$^{-1}$. Anal. Calcd for C$_{753}$H$_{1240}$N$_{52}$O$_{272}$: C, 58.83; H, 8.13; N, 4.74. Found: C, 58.81; H, 8.24; N, 4.51.

108-Cascade;methane[4]:(3-oxo-6-oxa-2 -azaheptylidyne):3-oxo-2-azapentylidyne )$^2$:propanol (21) was prepared (71%), as a hygroscopic white solid, from 108-ester 20 (750 mg, 48.8 μmol) via Procedure D: 374 mg; mp 71°–76°C.; $^1$H NMR (D$_2$O/p-dioxane/3.54 ppm) δ1.27 (br, CH$_2$CH$_2$CH$_2$, 216H), 1.49 (br, CH$_2$CH$_2$CH$_2$, 216H), 1.70 (br, $^{4°}$CNHCH$_2$CH$_2$CONH, 96H), 1.96 (br, $^{4°}$CNHCH$_2$CH$_2$CONH, 96H), 2.31 (br, OCH$_2$CH$_2$CONH, 8H), 3.20 (br, $^{4°}$C$_{Core}$CH$_2$, 8H), 3.38 (br, Ch$_2$OH, 216H), 3.49 (br, OCH$_2$CH$_2$CONH, 8H); $^{13}$C NMR (D$_2$O/p-dioxane/

66.4 ppm) δ25.3 (CH$_2$CH$_2$CH$_2$), 30.4 (CH$_2$CH$_2$CH$_2$) (30.8 ($^{4°}$CNHCH$_2$CH$_2$CONH), 36.7 (OCH$_2$CH$_2$CONH), 57.8, 57.7 ($^{4°}$CNH), 61.8 (CH$_2$OH), 67.8 ($^{4°}C_{Core}$CH$_2$), 69.2 (OCH$_2$CH$_2$CONH), 174.6 (CONH); IR 3343 (OH), 1653 (amide =CO), 1059 (C—O) cm$^{-1}$. Anal. Calcd for C$_{537}$H$_{1024}$N$_{52}$O$_{164}$: C, 59.53; H, 9.53; N, 6.72. Found: C, 59.37; H, 9.43; N, 6.79.

12-Cascade:methane[4]:(3-oxo-6-oxa-2-azaheptylidyne): N-tert-butoxycarbonyl)-propylamine (13). General Procedure E. A mixture of tetracid 1 (458 mg, 1.08 mmol), 1-HBT (612 mg, 4.53 mmol), and DCC (934 mg, 4.53 mmol) in DMF (20 mL) was stirred at 25° C. for 1 hour. Amine 4 (2.28 g, 4.54 mmol) in DMF (10 mL) was added to the mixture, which was stirred for 12 hours. Additional DCC (300 mg, 1.46 mmol) was added and the mixture was stirred for another 12 hours. After filtration of dicyclohexylurea, the solvent was removed in vacuo to give a residue, which was dissolved in EtOAc (50 mL), sequentially washed with cold aqueous HCl (10%), water, sat'd NaHCO$_3$, and brine. The organic phase was dried (MgSO$_4$), concentrated in vacuo, and chromatographed (SiO$_2$) eluting with 10% MeOH in EtOAc to furnish (56%) dodecacarbamate 12, as a spongy white solid: 1.43 g; mp 87°–89°C.; $^1$H NMR δ1.41 (s, CH$_3$ and CH$_2$CH$_2$CH$_2$, 132H), 1.67 (br, HN$^{4°}$CCH$_2$, 24H), 2.35 (br, OCH$_2$CH$_2$, 8H), 3.05 (br, CH$_2$NHBoc, 24H), 3.33 (br, $^{4°}$CCH$_2$O, 8H), 3.64 (br, OCH$_2$, 8H), 5.06 (s, NHBoc, 12H), 6.37 (very br, CONH, 4H); $^{13}$C NMR δ23.6 (CH$_2$CH$_2$CH$_2$), 28.4 (CH$_3$), 32.2 (HN$^{4°}$CCH$_2$, 37.5 (OCH$_2$CH$_2$), 40.8 (CH$_2$NHBoc), 58.2 ($^{4°}$CNH), 67.9 (4°CCH$_2$O), 69.5 (OCH$_2$), 78.9 (CMe$_3$), 156.1 (NHCOO), 170.8 (CONH); IR 3353 (NH), 1684 (C=O), 1456, (C—N), 1175 (C—O) cm$^{-1}$. Anal. Calcd for C$_{117}$H$_{220}$N$_{16}$O$_{32}$: C, 59.47; H, 9.38; N, 9.48. Found: C, 59.36; H, 9.23; N, 9.30.

12-Cascade:methane[4]:(3-oxo-6-oxa-2-azaheptylidyne):propylamine Hydrochloride (13). General Procedure F. A solution of dodecacarbamate 12 (1.28 g, 542 μmol) in 95% formic acid (10 mL) was stirred at 25° C. for 12 hours. After concentrating in vacuo, toluene (10 mL) was added and the solution was again evaporated in vacuo to remove azeotropically any residual formic acid. The crude formate salt was dissolved in aqueous 2% HCl (10 mL) and dialyzed (H$_2$O, 1 L, 12 h) using a 1,000 MWCO Spectra/Por® molecularporous membrane. Removal of the water in vacuo gave (37%) dodecaamine hydrochloride 13, as a hygroscopic, light yellow colored, glassy solid: 322 mg; $^1$H NMR (D$_2$O/p-dioxane/3.54 ppm) δ1.43 (br, CH$_2$CH$_2$CH$_2$, 24H), 1.56 (br, NH$^{4°}$CCH$_2$, 24 H), 2.36 (br, CH$_2$CONH, 8H), 2.81 (br, CH$_2$NH$_2$, 24 H), 3.20 (s, OCH$_2$, 8H), 3.48 (br, $^{4°}C_{Core}$CH$_2$O, 8 H); $^{13}$C NMR δ20.7 (CH$_2$CH$_2$CH$_2$), 30.8 (HN$^{4°}$CCH$_2$), 36.4 (CH$_2$CONH), 39.4 (CH$_2$NH$_2$), 44.9 (C$_{Core}$, 58.0 $^{4°}$CNH), 67.8 ($^{4°}C_{Core}$CH$_2$), 69.7 (OCH$_2$), 173.0 (CO); IR 3448 (NH$_3^+$), 2057 (NH$_3^+$overtone), 1648 (C=O), 1550 (NH$_3^+$bend) 1100 (C—NH$_3^+$0 cm$^-$.

36-Cascade:methane[4]:(3-oxo-oxa-2-azaheptylidyne):(3-oxo-2-azapentylidyne):N-(tert-butoxycarbonyl) propylamine (18) was prepared (68%), as a spongy white solid, from dodecaacid 11 (483 mg, 360 μmol), amine 4 (2.28 g, 4.54 mmol), 1-HBT (612 mg, 4.54 mmol), DCC (934 mg/300 mg, 4.54 mmol/1.46 mmol), and DMF (30 mL) via Procedure E: 1.76 g; mp 109°–112° C.; $^1$H NMR δ1.43 (s, CH$_3$ and CH$_2$CH$_2$CH$_2$, 396H), 1.66 (br, CH$_2$CH$_2$CH$_2$, 72H), 1 94 (br, HN$^{4°}$CCH$_2$CH$_2$CONH, 24 H), 2.15 (br, HN$^{4°}$CCH$_2$CH$_2$CONH, 24H), 2 35 (br, OCH$_2$CH$_2$, 8H), 3.05 (br, CH$_2$NHBoc, 72H), 3.29 (br, $^{4°}C_{Core}$CH$_2$O, 8H), 3.63 (br, OCH$_2$, 8H), 5.33 [very br, NHBoc, 28H (exchange)]; $^{13}$C NMR δ23.7 (CH$_2$CH$_2$CH$_2$), 28.5 (CH$_3$), 31.9 (br, HN$^{4°}$CCH$_2$CH$_2$CONH), 32.2 (CH$_2$CH$_2$CH$_2$), 37.6 (OCH$_2$CH), 40.9 (CH$_2$NHBOC), 58.1 ($^{4°}C_{Core}$CH$_2$O), 69.6 (OCH$_2$), 78.0 (CMe$_3$), 156.2 (NHCOO), 171.1 (CONH); IR 3350 (NH), 1697 (C=O), 1455 (C—N), 1172 (C—O) cm$^{-1}$. Anal. Calcd for C$_{357}$H$_{664}$N$_{52}$O$_{92}$: C, 59.91; H, 9.35; N, 10.18. Found: C, 59.97; H, 9.19; N, 9.99.

36-Cascade:methane[4]:(3-oxo-6-oxa-2-azaheptylidyne):(3-oxo-2-azapentylidyne):propylamine hydrochloride (19) was prepared from (49%), as a hygroscopic, light yellow colored, glassy solid, from 36-carbamate 18 (1.61 g, 225 μmol) via Procedure F: 530 mg; m; >182° C. (dec); $^1$H NMR (D$_2$O/p-dioxane/3.54 ppm) δ1.43 (br, CH$_2$CH$_2$CH$_2$, 72H), 1.57 (br, CH$_2$CH$_2$CH$_2$ 72H), 1.74 (br, HN$^{4°}$CCH$_2$CH$_2$CONH, 24H), 2.05 (br, HN$^{4°}$CCH$_2$CH$_2$CONH, 24H), 2.37 (br, OCH$_2$CH$_2$, 8H), 2.81 (br, CH$_2$NH$_3^+$; 72H), 3.23 (br $^{4°}C_{Core}$CH$_2$O, 8 H), 3.50 (br, OCH$_2$, 8H); $^{13}$C NMR (D$_2$O/p-dioxane/66.4 ppm) 20.8 (CH$_2$CH$_2$CH$_2$), 30.8 (br, CH$_2$CH$_2$CH$_2$ and HN$^{4°}$CH$_2$CH$_2$CONH), 36.5 (OCH$_2$CH$_2$), 39.6 (CH$_2$NH$_3^+$) 44.9 ($^{4°}C_{Core}$), 58.1 ($^{4°}$CNH), 67.9 ($^{4°}C_{Core}$CH$_2$O), 69.6 (br, OCH$_2$), 173.1 (OCH$_2$CH$_2$CONH), 175.3 (CONH); IR 3448 (NH$_3^+$) 2054 (NH$_3^+$overtone), 1646 (C=O), 1548 (NH$_3^+$ bend), 1098 (C—NH$_3^+$) cm$^{-1}$.

108-Cascade:methane[4]:(3-oxo-6-oxa-2-azaheptylidyne):(3-oxo-2-azapentylidyne)$^2$: N-tert-butoxycarbonyl-)propylamine (24) was prepared (70%), as a spongy white solid, from 36-acid 17 (491 mg, 120 μmol), amine 4 (2.28 g, 4.45 mmol), 1-HBT (612 mg, 4.45 mmol), DCC (934 mg/300 mg, 4.53 mmol/1.46 mmol), and DMF (30 mL) via Procedure E: 1.81 g; mp 119°–123° C.; $^1$H NMR δ1.43 (s, CH$_3$ and CH$_2$CH$_2$CH$_2$, 1188H), 1.66 (br, CH$_2$CH$_2$CH$_2$, 216H), 3.06 (br, CH$_2$NHBoc, 216H), 5.33 (very br, NHBoc, exchange); $^{13}$C NMR δ23.7 (CH$_2$CH$_2$CH$_2$), 28.5 (CH$_3$, 31.9 (br, HN$^{4°}$CCH$_2$CH$_2$CONH), 32.2 (CH$_2$CH$_2$CH$_2$), 40.9 (CH$_2$NHBoc), 58.1 (br, $^{4°}$CNH), 78.9 (CMe$_3$), 156.2 (NHCOO), 173.0 (br, CONH), IR 3337 (NH), 1698 (C=O), 1455 (C—N), 1170 (C—O) cm$^{-1}$. Anal. Calcd for C$_{1077}$H$_{1996}$N$_{160}$O$_{272}$: C, 60.05; H, 9.34; N, 10.40. Found: C, 60.11; H, 9.16; N. 10.32.

108-Cascade:methane[4]:(3-oxo-6-oxa-2-azaheptylidyne):(3-oxo-2-azapentylidyne)$^2$propylamine hydrochloride (25) was prepared (53%), as a hygroscopic, light yellow colored, glassy solid, from 108-carbamate 24 (1.66 g, 77.1 μmol) via Procedure F: 593 mg; mp>198° C. (dec); $^1$H NMR (D$_2$O/p-dioxane/3.54 ppm) δ1.44 (br, CH$_2$CH$_2$CH$_2$, 216H), 1.58 (br, CH$_2$CH$_2$CH$_2$, 216H), 1.73 (br, HN$^{4°}$CCH$_2$CH$_2$CONH, 96 H), 2.05 (br, HN$^{4°}$CCH$_2$CH$_2$CONH, 96H), 2.38 (br, OCH$_2$CH$_2$, 8H), 2.82 (br, CH$_2$NH$_3^+$, 216H), 3.21 (br, $^{4°}C_{Core}$CH$_2$O,8H), 3.49 (br, OCH$_2$, 8H); $^{13}$C NMR (D$_2$O/p-dioxane/66.4 ppm) δ20.8 (CH$_2$CH$_2$CH$_2$), 30.8 (br, CH$_2$CH$_2$CH$_2$ and HN$^{4°}$CH$_2$CH$_2$CONH), 36.5 (OCH$_2$CH$_2$), 39.6 (CH$_2$NH$_3^+$), 45.4 (br, $^{4°}C_{Core}$), 58.1 (br, $^{4°}$CNH) 68.0 (br, C$_{Core}$CH$_2$O), 69.7 (br, OCH$_2$), 175.4 (CONH); IR 3438 (NH$_3^+$), 2060 (NH$_3^+$overtone), 1646 (C=C), 1545 (NH$_3^+$bend), 1103 (C—NH$_3$) cm$^{-1}$.

The invention has been described in an illustrative manner, and it is to be understood the terminology used is intended to be in the nature of description rather than of limitation.

Obviously many modifications and variations of the present invention are possible in light of the above teachings. Therefore, it is to be understood that within the scope of the appended claims, the invention may be practiced otherwise than as specifically described.

REFERENCES 1. (a) Mittal, K. et al. in *Micellization. Solubilization, and Microemulsions*, Mittal, K. L., Ed.; Plenum Press, New York, 1977; (b) Tanford, C. in *The Hydrophobic Effect: The Formation of Micelles and Biological Membranes*, 2nd Ed., Wiley-Interscience, New York, 1980; (c) Ringsdorf, H. et al., *Angew. Chem. Int. Ed. Engl.* 1988, 27, 113–158.
2. Menger, F. *Angew, Chem. Int, Ed. Engl.* 1991, 30, 1086–1099.
3. (a) Mekelburger, H., Jaworek, W., Vögtle, F. *Angew. Chem. Int. Ed. Engl.* 1992, 31, 1571–1576 (b) Buhlin, E., Wehner, W., Vögtle, F., *Synthesis*, 1978, 155.
4. Newkome, G. R., Moorefield, C. N., Baker, G. R. *Adrichimca Acta* 1992, 25, 31–38.
5. Newkome, G. R., Moorefield, C. N., Baker, G. R., Johnson, A. L., Behera, R. K. *Angew Chem. Int. Ed. Engl.* 1991, 30, 1176.
6. Newkome, G. R., Moorefield, C. N., Baker, G. R., Saunders, M. J., Grossman, S. H. *Angew Chem. Int, Ed. Engl.* 1991, 30, 1178.
7. (a) Tomalia, D. A., et al., *Macromolecules* 1987, 20, 1167–1169; (b) Tomalia, D. A., et al., *Macromolecules* 1986, 19, 2466; Tomalia, D. A., et al., *J. Am. Chem. Soc.* 1987, 109, 1601–1603.
8. Pessi, A., Bianchi, E., Bonelli, F. Chiappinelli, L. *J. Chem. Soc. Chem. Commun.* 1990, 8–9.
9. Padias, A. B., Hall, H. K. Jr., Tomalia, D. A., McConnell, J. R. *J. Org. Chem.* 1987, 52, 5305–5312.
10. Bochkov, A. F., et al., *Izv. Akad. Nauk SSSR, Ser. Khim.* 1989, 2395.
11. Rengan, K., et al. *J. Chem. Soc., Chem. Commum.* 1990, 1084–1085.
12. Uchida, H., et al., *J. Am. Chem. Soc.* 1990, 112, 7077–7079.
13. Bochkarev, M. N., et al., *J. Organomet. Chem. (USSR)* 1987, 195.
14. Wooley, K. L., et al., *J. Chem. Soc. Perkin Trans.* 1 1991, 1059–1075; Hawker, C. J., Frechet, J. M. J. *J. Am. Chem. Soc.* 1990, 112, 7638–7647; *Macromolecules* 1990, 23, 4276–4729; *J. Chem. Soc., Chem. Commun.* 1990, 1010.
15. Rajca, A. *J. Org. Chem.* 1991, 56, 2557–2563; *J. Am. Chem. Soc.* 1990, 5890, 5889–5890.
16. Kim, Y. H., Webster, O. W. *J. Am. Chem. Soc.* 1990, 112, 4592.
17. Miller, T. M., Neenan, T. X. *Chem. Mater.* 1990, 2, 346.
18. Shahlai, K., Hart, H. *J. Am. Chem. Soc.* 1990, 112, 3687–3688; *J. Org. Chem.* 1990, 55, 3412.
19. Moore, J. S., Xu, Z. *Macromolecules* 1991, 24, 5893–5894.
20. Lakowicz, J. R., Cherek, H., Maliwal, B. P. *Biochem.* 1985, 24, 376–383.
21. Shinkai, S., et al., *J. Am. Chem. Soc.* 1986, 108, 2409; Brooker, L. G. S., Sprague, R. H. *J. Am. Chem. Soc.* 1941, 63, 3214.
22. Menger, F. M. Takeshita, M., Chow, J. F. *J. Am. Chem. Soc.* 1981, 103, 5938–5939.
23. Saunders, M. J., et al., planta 1981, 152, 272–281.
24. Menger, F. M., Takeshita, M., Chow, J. F. *J. Am. Chem. Soc.* 1981, 103, 5938–5939.
25. Newkome, G. R., et al., *Macromolecules* 26, 2394–2396, 1993.
26. de Gennes, P.-G., et al., *J. Phys. Lett.* 1983, 44, 351.
27. Schore, N. E., *Chemical Reviews* 1988, 88, 1081–1119.
28. March, J., *Adv. Org. Chem.*, 1985, 3rd Ed., pp. 237–301.
29. Newkome, G. R., Moorefield, C. N. *Polymer Preprints* 1993, 34, 75 (Abstr).
30. Newkome, G. R. et al., Unpublished results (1993).
31. Nicolas, K. M. et al., in "Transition Metal Organometallics in Organic Synthesis", Vol II, Alper, ed., Academic Press, New York (1978).
32. Nicolaou, K. C. et al., *J. Am. Chem. Soc.* 113:3106–3114 (1991).
33. Nicholas, K. M. et al., *Tetrahedron Lett.*, 3475–3478 (1971).
34. (a) Exon, C. et al., *J. Am. Chem. Soc.*, 105:2477–2480 (1983) (b) Knudsen, M. J. et al., *J. Org. Chem.*, 49:5025 (1984) (c) Magnus, P. et al., *J. Am. Chem. Soc.*, 110:6921–6925 (1988) (d) Nicholas, K. *Acct. Chem. Res.* 20:214–221 (1987).
35. Newkome, G. R. et al., in "Contemporary Heterocyclic Chemistry", Wiley-Interscience, New York (1982).
36. Distances were determined from extended conformations of modeled Micellanes using Quanta molecular modeling software from Polygen Corp.
37. Newkome, G. R. et al., *J. Am. Chem. Soc.*, 96:617 (1974).
38. Bradley, J. S. et al., *J. Am. Chem. Soc.*, 113:4016 (1991).
39. (a) Kauffman et al., *A. chem. Bet.* 109:3864 (1976). (b) Newkome, G. R. et al., *J. Org. Chem.*, 47:4116 (1982) (c) Pilper, P. J., *The Eur. J. Med. Chem. Chim. Ther.*, p. 399 (1984).
40. Newkome, G. R. et al., *J. Organometal. Chem.*, 198: 225 (1980).
41. Newkome, G. R., *J. Org. Chem.*, 54: 5105 (1989).
42. Lee, H. W., Dissertation, Louisiana State University (1983).
43. Tomasik, P. et al., in "Pyridine Metal Complexes", *The Chemistry of Heterocyclic Compounds*, Part 6A-C, Interscience, Newkome and Strekowski, editors, New York (1985).
44. (a) Ketz, H. et al., *Tetrahedron Lett.*, 31:4003–4006 (1990) (b) Mina, M. et al., *Tetrahedron Lett*, 31:2247 (1990) (c) Nemoto H. et al., *J. Org. Chem.* 57:437 (1992).
45. Newkome, G. R. et al., *Polymer Preprints*, 1993, 34, 75.
46. Akitt, J. W., *J. Mag. Reson.*, 1970, 3, 411–414.
47. Bruson, H. A. et al., *J. Am. Chem. Soc.* 64, 23 (1943).
48. Newkome, G. R. et al., *Macromolecules*, 26, 2394–2396 (1993).
49. Klausner, Y. S. et al., *Synthesis* 453–463 (1972).
50. DeTar, D. F. et al., *J. Am. Chem. Soc.* 88:5, 1024–1030 (1966).
51. Konig, W. et al., *Chem. Ber.* 103,788–798 (1970).
52. Morris, K. F. et al., *J. Am. Chem. Soc.* 115, 4291 (1993).
53. Gibbs, S. J. et al., *J. Magn. Reson.* 93, 395–402 (1991).
54. Gibbs, S. J. et al., *J. Magn. Reson.* 94, 165–169 (1991).
55. Stejskal, E. O. et al., *J. chem. Phys.* 42(1), 288–292 (1965).
56. Kellomaki, A., *Chemical Abstracts*, vol. 83, no. 19, 170021p, (1975)
57. Moorefield, C. N. *Dissertation*, (1991)

What is claimed is:

1. A method of preparing a unimolecular micelle by forming a core atom having a plurality of flexible branching arms extending therefrom and terminating each arm with a hydrodynamic reactive group (a) forming a first tier by amidating a tetracid core with a branched amine moiety wherein terminator of the branches are protected from the amidation under peptide coupling conditions;

(b) deprotecting the termination of the branches;

(c) repeating step (a) to form additional tiers; and (d) finally terminating the branches with a hydrodynamically reactive group.

2. A method of claim 1 wherein said terminating step is further defined as coupling an acid terminated branch with an acetate terminated monomer to provide acetate terminated branches and transesterifying the acetates to form alcohol terminators.

3. A method of claim 1 wherein said terminating step is further defined a coupling an acid terminated branch with a carbonates terminated monomer to provide carbonate terminated branches and treating the carbonate with acid to form amine terminations.

4. A method of claim 1 further including the step of modifying the flexibility of the arms to modify the extent to which the arm will extend.

* * * * *